United States Patent [19]
Clark et al.

[11] Patent Number: 5,423,322
[45] Date of Patent: Jun. 13, 1995

[54] TOTAL COMPLIANCE METHOD AND APPARATUS FOR NONINVASIVE ARTERIAL BLOOD PRESSURE MEASUREMENT

[75] Inventors: Justin S. Clark, Salt Lake City; Shuxing Sun, Sandy, both of Utah

[73] Assignee: Medical Physics, Inc., Salt Lake City, Utah

[21] Appl. No.: 227,680

[22] Filed: Apr. 14, 1994

Related U.S. Application Data

[63] Continuation of Ser. No. 756,194, Sep. 6, 1991, abandoned, which is a continuation-in-part of Ser. No. 291,769, Dec. 29, 1988, Pat. No. 5,111,817.

[51] Int. Cl.⁶ .............................................. A61B 5/021
[52] U.S. Cl. .................................. 128/672; 129/666; 129/667; 129/694
[58] Field of Search ................................ 128/633–635, 128/664–667, 672, 677, 679–683, 687–690, 694

[56] References Cited

U.S. PATENT DOCUMENTS

| | | |
|---|---|---|
| 3,412,729 | 11/1968 | Smith, Jr. |
| 3,903,872 | 9/1975 | Link. |
| 3,920,004 | 11/1975 | Nakayama. |
| 4,009,709 | 3/1977 | Link et al. |
| 4,074,711 | 2/1978 | Link et al. |
| 4,105,021 | 8/1978 | Williams et al. |
| 4,154,238 | 5/1979 | Link. |
| 4,174,707 | 11/1979 | Link et al. |
| 4,266,554 | 5/1981 | Hamaguri. |
| 4,271,843 | 6/1981 | Flynn. |
| 4,349,034 | 9/1982 | Ramsey, III. |
| 4,446,871 | 5/1984 | Imura. |
| 4,653,498 | 3/1987 | New, Jr. et al. |
| 4,685,464 | 8/1987 | Goldberger et al. |
| 4,714,080 | 12/1987 | Edgar, Jr. et al. |
| 4,759,369 | 7/1988 | Taylor. |
| 4,770,179 | 9/1988 | New, Jr. et al. |
| 4,776,339 | 10/1988 | Schreiber. |
| 4,805,623 | 2/1989 | Jöbsis. |
| 4,807,631 | 2/1989 | Hersh et al. |
| 4,825,872 | 5/1989 | Tan et al. |
| 4,825,879 | 5/1989 | Tan et al. |
| 4,832,484 | 5/1989 | Aoyagi et al. |
| 4,834,107 | 5/1989 | Warner. |
| 4,846,183 | 7/1989 | Martin. |
| 4,846,189 | 7/1989 | Sun. |
| 4,883,055 | 11/1989 | Merrick. |
| 4,889,133 | 12/1989 | Nelson et al. |
| 5,078,136 | 1/1992 | Stone et al. |
| 5,111,817 | 5/1992 | Clark et al. |
| 5,140,990 | 8/1992 | Jones et al. |

FOREIGN PATENT DOCUMENTS 0227119 12/1986 European Pat. Off.

OTHER PUBLICATIONS

Mandelson, Y. (1988) "Design and Evaluation of a New Reflectance Pulse Oximeter Sensor," *Medical Instrumentation*, vol. 22, No. 4, pp. 167–173.

(List continued on next page.)

Primary Examiner—Angela D. Sykes
Attorney, Agent, or Firm—Thorpe, North & Western

[57] ABSTRACT

A system and method for automatically and noninvasively monitoring the blood pressure of a subject. The volume changes of an artery, such as a digital artery or the temporal artery, are detected by a photoplethysmograph. The volume changes are then used to determine the blood pressure and the blood pressure waveform, of the subject. The model used to relate the volume of the artery to the pressure contained within the artery is referred to as the total compliance model. The total compliance model determines the compliance of each patient's artery which is being used as a sensing site. The compliance information is then used to determine the blood pressure at any particular point in time to the detected volume of the artery. Thus, the present invention can be reliably and accurately used with patients which have abnormal blood pressure levels and waveforms which heretofore could not be accurately measured using previous noninvasive methods and apparatus that assumed once the mean pressure for a patient was determined, the systolic and diastolic pressure could be found by applying fixed ratio techniques to detected changes in arterial volume.

32 Claims, 10 Drawing Sheets

OTHER PUBLICATIONS

Mandelson, Y. "Theory and Development of a Transcutaneous Reflectance Oximeter System for Noninvasive Measurements of Arterial Oxygen Saturation.".

Ramsey, M. (1979) "Noninvasive Automatic Determination of Mean Arterial Pressure," *Med. & Biol. Eng. & Comput.*, vol. 22, pp. 11–18.

Hardy, H. H. and Collins, R. E. (1982), "On The Pressure-Volume Relationship in Circulatory Elements," *Med. & Biol. Eng. & Comput.*, vol. 20, pp. 565–570.

Messerli, F., et al. (1985), "Osler's Maneuver and Pseudohypertension," *The New England Journal of Medicine*, vol. 312, No. 24, pp. 1548–1551.

Messerli, F., "The Age Factor in Hypertension," *Hospital Practice*, Jan. 15, 1986 Edition, pp. 103–112.

Messerli, F. (1986), "Osler's Maneuver, Pseudohypertension, and True Hypertension in the Elderly," *The American Journal of Medicine*, vol. 80, pp. 906–910.

TOTAL COMPLIANCE METHOD AND APPARATUS FOR NONINVASIVE ARTERIAL BLOOD PRESSURE MEASUREMENT

1. Related Applications

This application is a continuation of U.S. patent application Ser. No. 07/756,194, filed Sep. 6, 1991, now abandoned, entitled Total Compliance Method and Apparatus for Noninvasive Arterial Blood Pressure Measurement which is a continuation-in-part of U.S. patent application Ser. No. 07/291,769, filed Dec. 29, 1988, now U.S. Pat. No. 5,111,817, entitled Noninvasive System and Method for Enhanced Arterial Oxygen Saturation Determination and Arterial Blood Pressure Monitoring which is now incorporated herein by reference. It will be understood that the system and method disclosed therein can be readily used in conjunction with the invention disclosed herein.

BACKGROUND

2. The Field of the Invention

This invention relates to apparatus used to determine blood pressure of a subject. More particularly, the present invention relates to methods and apparatus which are used to noninvasively and continually determine a subject's blood pressure.

3. The Prior Art

Out of all of a patient's physiological signs which can be monitored by medical practitioners, the physiological parameter which practitioners would prefer to have monitored for critically ill patients, if only one physiological sign could be monitored, would be the patient's blood pressure. Cardiologists, anesthesiologists, internists, and other practitioners dealing in many areas of medicine consider blood pressure measurements to be extremely valuable. Investigators in the basic life sciences often measure blood pressure under a wide variety of circumstances.

There are many different ways to measure arterial blood pressure. These include invasive (direct) and noninvasive (indirect) methods as well as continual and intermittent methods.

Intra-arterial catheterization is a very invasive and direct method of arterial blood pressure measurement. Intra-arterial catheterization, however, is the most reliable and accurate method for blood pressure measurement because it provides direct and continuous monitoring of the pressure actually in a major artery such as the descending aorta. The risk, however, of complications such as thrombosis, embolism, and infections limits the use of intra-arterial catheterization for blood pressure monitoring to those situations where the benefits of its use outweigh the risk. Such situations include, for example, monitoring of critically ill patients in an intensive care unit or during surgical procedures in an operating room. Because of the disadvantages of direct invasive blood pressure monitoring techniques, many noninvasive techniques for the monitoring of arterial blood pressure have been proposed in the art.

In 1834, the first indirect measurement of human blood pressure was made by Herisson. Herisson's technique used a sphygmomanometer that applied a counterpressure (referred to as Pc) to the radial artery of the arm. Herisson determined a subject's systolic pressure (referred to as Ps) by noting the amount of Pc required to eliminate arterial pulsation. Still Herisson's method had several drawbacks which resulted in inaccurate measurements and the method could only determine Ps.

Later, Riva-Rocci introduced an air-inflated arm-occluding cuff which improved the determination of Pc. Still later, Korotkoff proposed the auscultatory method of indirect blood pressure measurement which provided for the determination of diastolic pressure (referred to as Pd) in addition to determining Ps.

In the commonly practiced modern auscultatory method, the pressure of the air inflated cuff around the subject's arm (Pc) is first raised quickly until the occlusion of the brachial artery occurs. A stethoscope placed over a brachial artery below the cuff is used to listen to the Korotkoff sounds (the sounds made as blood passes through a partially occluded artery) as the Pc is gradually released. Ps is taken to be equal to the Pc corresponding to the occurrence of the first Korotkoff sound; Pd is taken to be equal to the Pc which corresponding to the fourth or fifth Korotkoff sound.

The accuracy of the auscultatory method is limited by the arbitrary nature of the relationship between the Korotkoff sounds and the corresponding pressure values as well as the skill of the person carrying out the method. In a subject having normal blood pressure, Ps values determined by the auscultatory method tend to be low (about 3–4 mmHg) with a standard deviation (SD) of 8 mmhg, while Pd values tend to be high (about 8 mmHg) with a SD of 8 mmHg. Other recognized major disadvantages of the auscultatory method is that its accuracy degrades severely with hypotension and obesity. It is also unreliable in infants and children.

Another method of making noninvasive blood pressure measurements is the oscillometric method. The oscillometric method of blood pressure determination attempts to overcome the drawbacks which accompany the use of the auscultatory method. The oscillometric principle states that there is a Pc which causes maximum oscillation of the Pc. Furthermore, the oscillometric principle states that when the maximum oscillation of Pc is obtained, Pc is equal to the subject's mean arterial pressure (referred to as Pm).

The correspondence between the maximum oscillation of Pc and Pm, however, has been shown to be dependent on pulse pressure (Ps−Pd) with the deviation of measured Pm from actual Pm increasing with increasing pulse pressure. Even though the oscillometric principle has been recognized for almost a century, the development of the oscillometric method for measuring Ps and Pd has occurred much more recently.

From studies published in 1982, comparing the auscultatory method and the oscillometric method in human subjects, it was found that Ps was equal to the Pc corresponding to oscillation amplitudes in the range of 0.45 to 0.57 of maximum oscillations (corresponding to Pm); Pd was found to equal the Pc corresponding to the oscillation amplitudes in the range of 0.75 to 0.86 of maximum oscillations. In a study using dogs, in which the direct arterial catheterization method was used as a reference, it was found that the systolic and diastolic ratios varied from about 0.43 to 0.73 and from about 0.69 to 0.83 of maximum oscillation, respectively.

It has hitherto been seldom recognized that the measurement of Pm using the oscillometric method is likely to be inaccurate, and increasingly so in the case of young, obese, hyper- or hypo-tensive, or other patients, which are abnormal in some respect. In the previously used oscillometric method, Pd and Ps are assumed to be some fixed ratio of the changes in arterial volume which are detected by some apparatus. Upon close examination of actual patients, as explained further below, not only is the determination of Pm often inaccurate, but the assumption that Pd and Ps are a fixed ratio does not hold in cases of abnormal blood pressure waveforms or other abnormal conditions.

Other methods for noninvasive continuous arterial blood pressure measurement, such as the volume clamp method, also present their own disadvantages and difficulties. In recent years, devices which are designed to automatically and noninvasively measure blood pressure have been introduced. Both the volume clamp and the oscillometric methods of blood pressure measurement have been used in mechanical, automated devices to noninvasively provide blood pressure determinations.

One of the automated blood pressure measuring devices which has been introduced, and which uses the oscillometric principle, is marketing under the trademark DINAMAP ™ and available from Critikon. Another automated blood pressure measuring device which is now available is marketed under the trademark FINAPRES ™. The FINAPRES ™ device uses the volume clamp method of blood pressure determination.

Both the DINAMAP ™ device and the FINAPRES ™ device have serious drawbacks and disadvantages, most of which are inherent in the method of blood pressure determination used thereby. For example, it has been determined that these noninvasive blood pressure measuring techniques produce results which significantly differ from measurements obtained by direct catheterization in anesthetized surgical patients. In hypertensive patients, systematic errors in Ps as large as $-53.3$ mmHg have been reported. In hypotensive patients, systematic errors in Pd as large as 16.6 mmHg have been reported. It has been reported that the DINAMAP ™ device routinely underestimates Ps in hypertensive patients and overestimates Pd in hypotensive patients.

In an effort to overcome the problems associated with frequent inflation of arm cuffs, devices applying pressure to a finger (i.e., a digital artery) have been developed. Alternative schemes using the oscillometric principal have been developed which permit finger site application with results comparable to those of the oscillometric method applied to other sites on the body. The finger site oscillometric method uses photoelectric plethysmography to provide a volume oscillogram (a series of pulse volumes as a function of Pc).

Critically, the oscillometric method relies upon assumptions and empirical data which may not be accurate under the most important circumstances, i.e., in the hypotensive or hypertensive patient. These assumptions include the assumption that Pd and Ps are always a fixed ratio of the detected changes in arterial volume in all patients; an assumption which heretofore has not been recognized as false in many important circumstances. Thus, it would be a great advance in the art to provide a noninvasive blood pressure measuring system and method which produces accurate measurements for both normal and abnormal subjects.

BRIEF SUMMARY AND OBJECTS OF THE INVENTION

In view of the above described state of the art, the present invention seeks to realize the following objects and advantages.

It is a primary object of the present invention to provide a noninvasive blood pressure measurement system and method which is more accurate on abnormal, as well as normal, patients than previously available noninvasive blood pressure monitoring devices.

It is another object of the present invention to provide a noninvasive blood pressure measurement system and method which utilizes a physiologically based model rather than an empirically based model.

It is a further object of the present invention to provide a noninvasive blood pressure measurement system and method which results in little interpatient variability.

It is yet another object of the present invention to provide a noninvasive blood pressure measurement system and method which allows placement on any number of sites on the patient, such as a finger, and is suitable for long term continuous monitoring.

It is still another object of the present invention to provide a noninvasive blood pressure measurement system and method which utilizes physiologically determined parameters developed for each patient depending on the patient's arterial compliance in order to provide greater accuracy with significantly less interpatient variability than previous methods and devices.

These and other objects and advantages of the invention will become more fully apparent from the description and claims which follow, or may be learned by the practice of the invention.

The present invention provides a system and method for automatically and noninvasively monitoring the blood pressure of a subject. Most critically, the system and method of the present invention is well suited to measuring the blood pressure of a patient being treated for an illness or trauma, such patients often having abnormal blood pressure levels or abnormal blood pressure waveforms. The present invention provides much more accurate noninvasive determinations of systolic blood pressure, diastolic blood pressure, mean blood pressure in patients with abnormal blood pressure than previous apparatus and methods. The present invention can also provide a representation of the patient's blood pressure waveform.

Preferred embodiments of the present invention include means for noninvasively detecting volume changes in an artery of the patient. Such changes can preferably be detected by providing a light means, such as an LED, which emits a light into the body part containing an artery, and a detection means, such as a photodetector, which receives the light which is either reflected from, or transmitted through, the body part. By detecting the amount of light which is absorbed by the artery, which varies with each heart beat, the volume of the artery can be assessed.

Based upon a model relating the pressure within an artery to the volume of the artery (i.e., the P-V relationship), the pressure within the artery can be measured by the detected changes in the volume of the artery. The model used by the present invention is referred to as the total compliance model. The total compliance model determines the compliance of each patient's artery which is being used as a sensing site. In contrast, previous apparatus and methods have assumed, particularly incorrectly in the case of some abnormal patients, that a patient's diastolic and systolic blood pressures can be determined by applying fixed ratio techniques to detected changes in arterial volume. Rather than measuring the patient's mean blood pressure using oscillometric techniques and then assuming that the patient's diastolic pressure and systolic pressures are some fixed percentage or ratio in accordance with the detected changes in arterial volume, the total compliance model of the present invention determines the arterial compliance of the artery and uses the compliance information to determine the actual blood pressure, both for pressures above and below the mean blood pressure.

A processor means, which can be a general purpose microprocessor based machine or a dedicated computing apparatus, is included to coordinate the operation of the other system structures and to carry out the mathematical operations on the data collected from sensing the patient. A pressure means, preferably an inflatable air bladder, is included to apply a counterpressure to the body part, and the artery contained therein, in order to create an oscillogram for the patient. The blood pressure information is conveyed from the processor means via an output means to some device such as a display.

The present invention allows continuous or intermittent monitoring of a patient's blood pressure, including a blood pressure waveform, more accurately than with previous apparatus and methods. Since the compliance of each artery used to make measurements is individually determined, even patients which have abnormal blood pressure levels and waveforms are suitable for noninvasive blood pressure monitoring using the present invention. The present invention is also well suited to being used with a method, and as part of system, for noninvasive arterial oxygenation determinations.

BRIEF DESCRIPTION OF THE DRAWINGS

In order to better appreciate how the above-recited and other advantages and objects of the invention are obtained, a more particular description of the invention briefly described above will be rendered by reference to the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

General Discussion

As discussed above, the various models used by previously available noninvasive blood pressure measurement methods have been based upon empirically gathered data of the relationship between the pressure within an artery and the volume of the artery. Most prominent among these models is the use of a fixed ratio to arrive at Ps and Pd after Pm has been found using the oscillometric principle. Such models appear to provide useful results in many cases for normal patients.

As considered earlier, however, the empirically based fixed ratio model, as well as other models, fail to provide reliable results for hypotensive or hypertensive patients, or as will be explored more generally below, those patients having an abnormal oscillogram (blood pressure) waveform. Arguably, these patients are those which are in the greatest need of accurate and reliable noninvasive blood pressure measurement.

As explained in detail below, the present invention provides a more accurate and reliable system and method for noninvasively measuring blood pressure by using a physiologically based model for characterizing the relationship between an artery's volume and the pressure contained therein. By considering the arterial pressure-volume relationship for each patient, and that relationship over the entire range of measured volumes (i.e., from under Pd to over Ps), a heretofore unavailable, highly accurate, and reliable noninvasive blood pressure measurement system and method results. The blood pressure measurement method of the present invention is generally referred to as the "total compliance" method or model.

Figure 1:
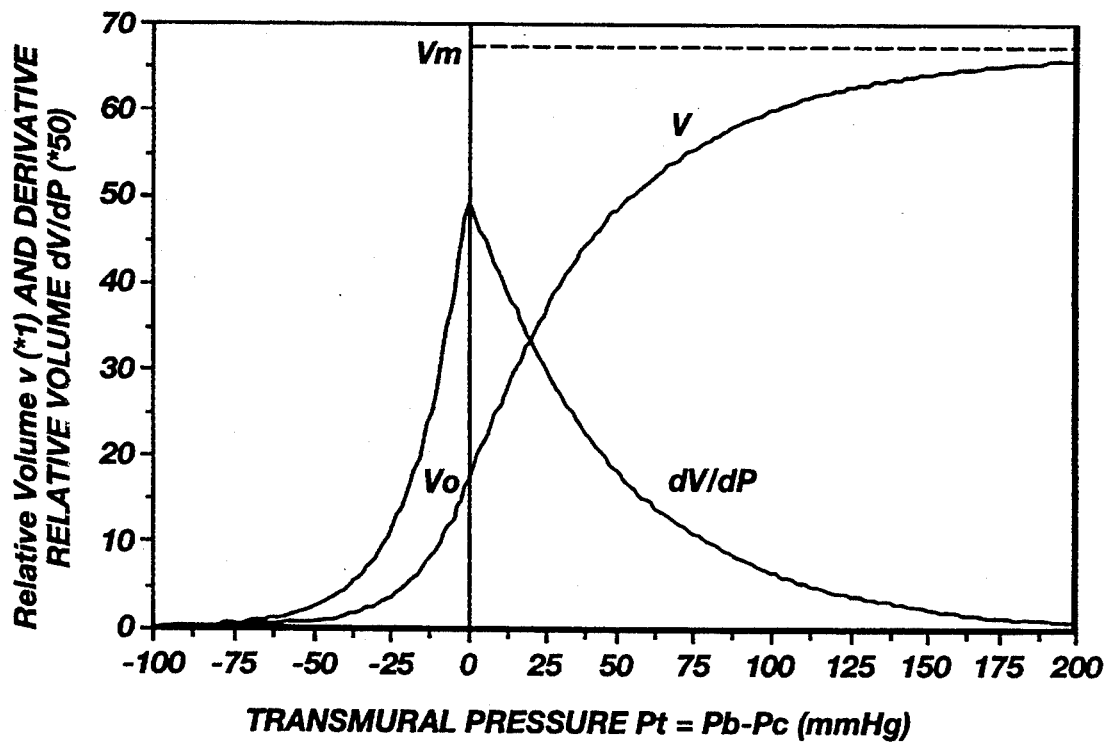
FIG. 1 is a chart showing the relationship between intra-arterial blood pressure and arterial volume.

Previous work in the art has studied the relationship between pressure and volume (P-V) for human arteries. In such work, generally attributed to Hardy and his coworkers and thus referred to as the "Hardy model," it has been assumed that the in vivo arterial P-V relationship can be represented as set forth in the chart of FIG. 1 where the relative volume of the artery is represented by the vertical axis and the transmural pressure (mmHg) (also referred to in the art as transluminal pressure) is represented by the horizontal axis. In FIG. 1, TC represents the total compliance model curve, Pb represents the intra-arterial blood pressure, Pc represents the counterpressure applied to the artery, Pt represents the transmural pressure, V represents the arterial volume, Vm represents the maximum volume of the artery, Vo represents the residual volume of the artery, and dV/dP represents the arterial compliance.

In FIG. 1, the volume curve to the right of zero transmural pressure ($P_T \geq 0$) is expressed by Equation (1)

$$V = V_o + (V_m - V_o)(1 e^{-kPT}) \tag{1}$$

and the volume curve to the left of zero transmural pressure ($P_T \leq 0$) is expressed by Equation (2)

$$V = V_o e^{k'P_T} \tag{2}$$

where Vm (maximum volume), Vo (residual volume), k (compliance index), and k' (also compliance index) are model parameters and PT is defined as $$P_T \equiv P_b - P_c \tag{3}$$

where Pb and Pc are the blood pressure and the counterpressure applied to the artery, respectively.

The physical constraint that the derivatives of Equations (1) and (2) be equal at $P_T = 0$ reduces the Hardy model to three independent parameters by establishing a relationship between the compliance indices k and k', given as follows.

Equating the derivatives of Equations (1) and (2) at $P_T = 0$ gives Equation (4)

$$\left.\frac{dV}{dP_T}\right|_{P_T=0} = (V_m - V_o) = V_o K' \tag{4}$$

which gives $$k' = \frac{V_m - V_o}{V_o} k \tag{5}$$

thereby providing a P-V model containing the three independent parameters k, Vm, and Vo.

Support for the right half of the model (Equation (1)) is widely available in the art. The addition of the left half of the pressure-volume model represented in FIG. 1 (Equation (2)), together with the Hardy pressure-volume model (illustrated by the right half of the chart in FIG. 1 and Equation (1)) is representative of the Total Compliance (TC) model of the arterial pressure-volume relationship utilized by the present invention.

Figure 2:
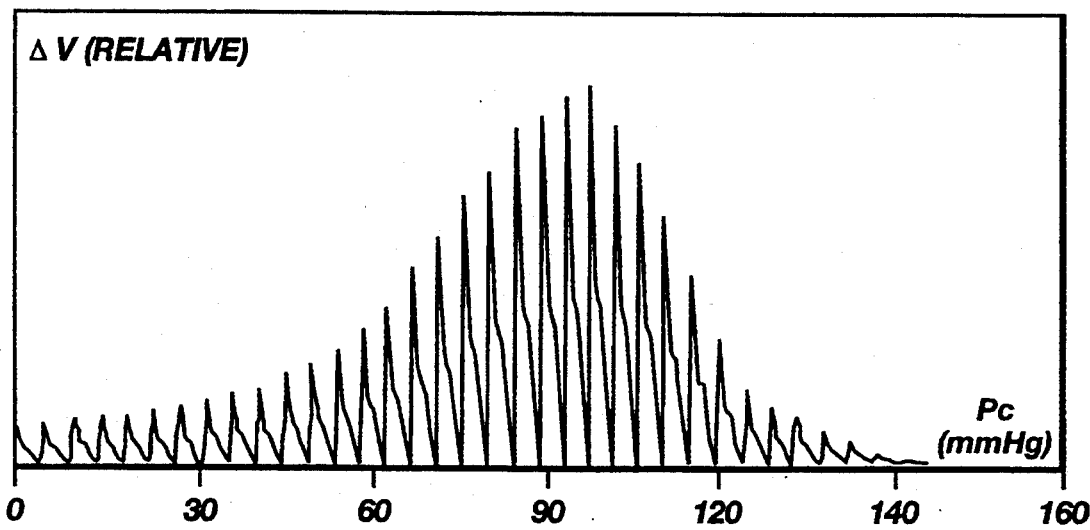
FIG. 2 is a chart showing the change in arterial volume as represented in an oscillogram as a function of counterpressure Pc on the artery.

FIG. 2 will be referred to next. FIG. 2 is a diagram showing a typical arterial volume oscillogram as a function of arterial counterpressure where $\Delta V$ represents pulse volume and Pc represents counterpressure. The total compliance model of the present invention utilizes pulse volume ($\Delta V$) of the volume oscillogram, as shown in FIG. 2, to generate the k, k', Vm, and Vo parameters of the total compliance model.

The arterial pressure measurements obtained in accordance with the present invention are also derived from the parameters already discussed. From Equations (1) and (3), the volumes of the artery at the systolic pressure (the systolic volume Vs) and at the diastolic pressure (the diastolic volume Vd) are given by $$V_s = V_o + (V_m - V_o)[1 - e^{-k(P_s - P_c)}] \tag{6}$$

$$V_d = V_o + (V_m - V_o)[1 - e^{-k(P_d - P_c)}] \tag{7}$$

V is then obtained in the range of $P_c \leq P_d$ by subtraction of Equation (7) from Equation (6) which gives $$\Delta V = (V_m - V_o)(e^{-kP_d} - e^{-kP_s})e^{kP_c} \tag{8}$$

For stable values of Ps and Pd, Equation (8) can be represented as $$\Delta V = A e^{kP_c} \tag{9}$$

where A is a constant given by $$A = (V_m - V_o)e^{-kP_d}(1 - e^{-k\Delta P}) \tag{10}$$

where $\Delta P$ is pulse pressure given by $$\Delta P = P_s - P_d \tag{11}$$

Following the same procedure for the range of $P_c \geq P_s$, $$\Delta V = A' e^{-k'P_c} \tag{12}$$

where A' is a constant given by $$A' = -V_o e^{k'P_d}(1 - e^{k'\Delta P}) \tag{13}$$

By fitting the pulse volume of the volume oscillogram to Equation (8) in the range of $P_c \leq P_d$, the constants A and k can be obtained. Likewise, constants A' and k' can be obtained by fitting the pulse volume of the volume oscillogram to Equation (12) in the range of $P_c \geq P_s$. With k and k' determined, the model parameters yet to be determined are Vo and Vm, which are represented independently in Equations (5), (10), and (13). However, the unknown pressure values Pd and $\Delta P$ also appear in Equations (10) and (13), which makes four unknowns contained in three independent equations. To obtain a fourth relationship, $\Delta V$ in the range of $P_d < P_c < P_s$ is used. In this range, Vs is given by Equation (1) and Vd is given by Equation (2). Subtraction gives $$\Delta V = V_o + (V_m - V_o)[1 - e^{-k(P_d + \Delta P - P_c)}] - V_o e^{k'(P_d - P_c)} \tag{14}$$

Equation (14) is the fourth independent relationship for extracting Vo, Vm, Pd, and $\Delta P$. Using the above four independent Equations (5, 10, 13, and 14), the total compliance model utilized by the present invention can be established and the desired pressure values (Ps and Pd) can be obtained. In Equation (14), maximum sensitivity can be obtained when Pc is given a value corresponding to maximum $\Delta V$. However, to minimize the influence of oscillogram noise, this relationship should be replaced with a relationship (using Equation (14)) which contains a least square best fit criterion for matching all the oscillogram data with the oscillogram prediction (by the best fit total compliance model) in the region of $P_d < P_c < P_s$ as described below.

First, division of Equation (10) by Equation (13) gives $$\frac{A}{A'} = \frac{V_m - V_o}{V_o} e^{-(k+k')P_d} \frac{1 - e^{-k\Delta P}}{e^{k'\Delta P} - 1} \tag{15}$$

and substitution of Equation (5) into this equation gives $$\frac{A}{A'} = \frac{k'}{k} e^{-(k+k')P_d} \frac{1 - e^{-k\Delta P}}{e^{k'\Delta P} - 1} \tag{16}$$

Rearranging Equation (16) gives $$P_d = \frac{1}{K + K'} \ln\left(\frac{A'k'}{Ak} \frac{1 - e^{-k\Delta P}}{e^{k'\Delta P} - 1}\right) = F(\Delta P) \tag{17}$$

where $F(\Delta P)$ is a function of $\Delta P$ as defined by Equation (17) which describes the internal relationship between Pd and $\Delta P$ of the total compliance model.

Second, Equation (10) can be represented as $$Vm - Vo = \frac{Ae^{kPd}}{1 - e^{-k\Delta P}} \quad (18)$$

and Equation (13) can be represented as $$Vo = \frac{A'e^{-k'Pd}}{e^{k'\Delta P} - 1} \quad (19)$$

Substituting Equations (18) and (19) into the fourth independent relationship of Equation (14) gives $$\Delta V = \frac{A}{1 - e^{-k\Delta P}} [e^{kPd} - e^{-k(\Delta P - Pc)}] + \quad (20)$$

$$\frac{A'}{e^{k'\Delta P} - 1} (e^{-k'Pd} - e^{-k'Pc})$$

Substituting Equation (17) of $F(\Delta P)$ into the above Equation (20) further gives $$\Delta V = \frac{A}{1 - e^{-k\Delta P}} [e^{kF(\Delta P)} - e^{-k(\Delta P - Pc)}] + \quad (21)$$

$$\frac{A'}{e^{k'\Delta P} - 1} (e^{-k'F(\Delta P)} - e^{-k'Pc}) \equiv G(\Delta P, Pc)$$

where $G(\Delta P, Pc)$ is a function of $\Delta P$ and Pc as defined by Equation (21) which describes the internal relationship between $\Delta V$ and $\Delta P$ of the total compliance model under the counterpressure Pc.

Third, a least square criterion can be defined between the true oscillogram data $\Delta V(Pc)$ and predicted oscillogram $G(\Delta P, Pc)$ of the total compliance model in the region of $Pd < Pc < Ps$. The criterion is given by $$J(\Delta P) = \sum_{Pc > Pd}^{Pc \leq Ps} [\Delta V(Pc) - G(\Delta P, Pc)]^2 \quad (22)$$

Minimize J by $dJ/d(\Delta P) = 0$ to give $$\sum_{Pc > Pd}^{Pc \leq Ps} [\Delta V - G] \frac{dG}{d(\Delta P)} = 0 \quad (23)$$

where $\Delta V$ stands for $\Delta V(Pc)$ and G for $G(\Delta P, Pc)$. From Equation (21) of $G(\Delta P, Pc)$, it is derived that $$\frac{dG}{d(\Delta P)} = \frac{Ak}{(1 - e^{-k\Delta P})^2} \left[ e^{kF}(1 - e^{-k\Delta P}) \frac{dF}{d(\Delta P)} - \right.$$

$$\left. e^{kF}e^{-k\Delta P} + e^{-k(\Delta P - Pc)} \right] -$$

$$\frac{A'K'}{(e^{k'\Delta P} - 1)^2} \left[ e^{-k'F}(e^{k'\Delta P} - 1) \frac{dF}{d(\Delta P)} + \right.$$

$$\left. e^{-k'F}e^{-k'\Delta P} - e^{k'(\Delta P - Pc)} \right]$$

where F stands for $F(\Delta P)$. From Equation (17) of $F(\Delta P)$, it is further derived that $$\frac{dF}{d(\Delta P)} = \frac{1}{K + K'} \left( \frac{ke^{-k\Delta P}}{1 - e^{-k\Delta P}} - \frac{k'e^{k'\Delta P}}{e^{k'\Delta P} - 1} \right) \quad (25)$$

$$e^{kF} = \left( \frac{A'k'}{Ak} \frac{1 - e^{-k\Delta P}}{e^{k'\Delta P} - 1} \right)^{\frac{k}{k+k'}} \quad (26)$$

$$e^{-k'F} = \left( \frac{A'k'}{Ak} \frac{1 - e^{-k\Delta P}}{e^{k'\Delta P} - 1} \right)^{\frac{k'}{k+k'}} \quad (27)$$

Substituting Equations (25), (26), and (27) into Equation (24) gives $$\frac{dG}{d(\Delta P)} = \frac{Ak}{(1 - e^{-k\Delta P})^2} \left\{ \left( \frac{A'k'}{Ak} \frac{1 - e^{-k\Delta P}}{e^{k'\Delta P} - 1} \right)^{\frac{k}{k+k'}} \left[ \frac{k}{k + K'} e^{-k\Delta P} - \frac{k'}{k + k'} e^{k'\Delta P} \frac{1 - e^{-k\Delta P}}{e^{k'\Delta P} - 1} - e^{-k\Delta P} \right] + e^{-k(\Delta P - Pc)} \right\} - \quad (28)$$

$$\frac{A'k'}{(e^{k'\Delta P} - 1)^2} \left( \frac{A'k'}{Ak} \frac{1 - e^{-k\Delta P}}{e^{-k\Delta P} - 1} \right)^{-\frac{k'}{k+k'}} \left[ -\frac{k'}{k + k'} e^{k'\Delta P} + \frac{k}{k + k'} e^{-k\Delta P} \frac{e^{k'\Delta P} - 1}{1 - e^{-k\Delta P}} + e^{k'\Delta P} \right] - e^{k'(\Delta P - Pc)} \right\}$$

and substituting Equations (26) and (27) into Equation (21) gives $$G(\Delta P, Pc) = \quad (29)$$

$$\frac{A}{1 - e^{-k\Delta P}} \left[ \left( \frac{A'k'}{Ak} \frac{1 - e^{-k\Delta P}}{e^{k'\Delta P} - 1} \right)^{\frac{k}{k+k'}} - e^{-k(\Delta P - Pc)} \right] +$$

$$\frac{A'}{e^{k'\Delta P} - 1} \left[ \left( \frac{A'k'}{Ak} \frac{1 - e^{k'\Delta P}}{e^{k'\Delta P} - 1} \right)^{\frac{k'}{k+k'}} \right]$$

Substituting Equations (28) and (29) finally gives the form of least square criterion $J'(\Delta P)$ as $$J(\Delta P) \equiv \sum_{Pc > Pd}^{Pc \leq Ps} \left( \Delta V - \left\{ \frac{A}{1 - e^{-k\Delta P}} \left[ \left( \frac{A'k'}{Ak} \frac{1 - e^{-k\Delta P}}{e^{k\Delta P} - 1} \right)^{\frac{k}{k+k'}} - e^{-k(\Delta P - Pc)} \right] + \right. \right. \quad (30)$$

$$\left. \left. \frac{A'}{e^{k'\Delta P} - 1} \left[ \left( \frac{A'k'}{Ak} \frac{1 - e^{-k\Delta P}}{e^{k'\Delta P} - 1} \right)^{\frac{k'}{k+k'}} - e^{-k'Pc} \right] \right\} \right)$$

-continued $$\left(\frac{Ak}{(1-e^{-k\Delta P})^2}\left\{\left(\frac{A'k'}{Ak}\frac{1-e^{-k\Delta P}}{e^{k'\Delta P}-1}\right)^{\frac{k}{k+k'}}\left[\frac{k}{k+k'}e^{-k'\Delta P}-\right.\right.\right.$$

$$\left.\left.\frac{k'}{k+k'}e^{k\Delta P}\frac{1-e^{-k\Delta P}}{e^{k'\Delta P}-1}-e^{-k\Delta P}\right]+e^{-k(\Delta P-Pc)}\right\}-$$

$$\frac{A'k'}{(e^{k'\Delta P})^2-1}\left\{\left(\frac{A'k'}{Ak}\frac{1-e^{-k\Delta P}}{e^{k'\Delta P}-1}\right)^{-\frac{k'}{k+k'}}\left[-\frac{k'}{k+k'}e^{k'\Delta P}+\right.\right.$$

$$\left.\left.\frac{k}{k+k'}e^{-k\Delta P}\frac{e^{k'\Delta P}-1}{1-e^{-k\Delta P}}-e^{k'\Delta P}\right]-e^{k'(\Delta P-Pc)}\right\}\right)=O$$

Equation (30) is the formula used in the total compliance model or the present invention. In Equation (30), $\Delta V$ (oscillogram data), Pc (cuff pressure), A and A' (total compliance model fit parameters to the oscillogram data), k and k' (total compliance model fit compliance indices to the oscillogram data) are available from the measurement data and calculations explained above.

Using a numerical method (Newton method, golden section method, etc.), the pulse pressure $\Delta P$ can be searched within pre-defined error limit of 0.5 mmHg. After $\Delta P$ is found, the diastolic pressure can be calculated from Equation (17). Consequently, the residual volume Vo (relative to the optical plethysmograph unit) can be calculated from Equation (19) and the maximum volume Vm (also relative to the optical plethysmograph unit) can be calculated from Equation (5). The systolic pressure Ps can be obtained by $\Delta P+Pd$ and the mean pressure can be obtained by the integration as described by Equation (32) provided below.

Figure 3:
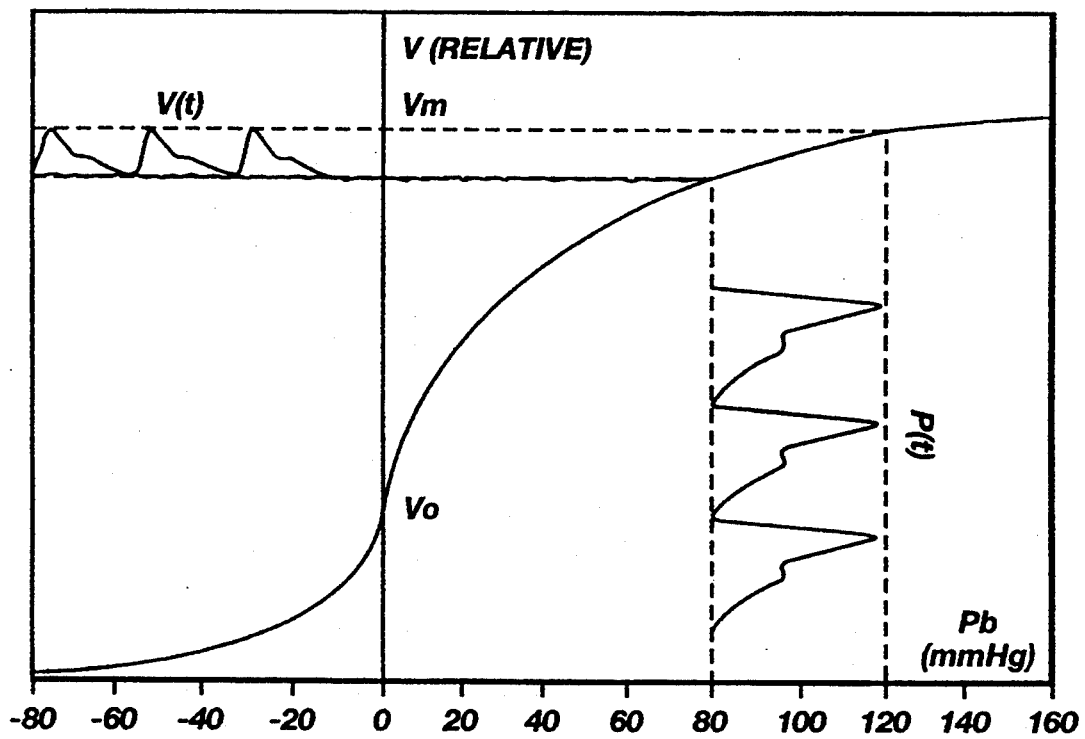
FIG. 3 is a chart showing the relationship of arterial pressure P(t) and arterial volume V(t).

With model parameters k, Vo, and Vm being established, the time representation of pressure waveform (P(t)) can then be constructed from the volume waveform (V(t)) at Pc=0, as shown in FIG. 3. FIG. 3 shows the relationship of P(t)V(t) at zero counterpressure. In FIG. 3, P(t) represents the pressure waveform, V(t) represents the volume waveform, t represents time, Pb represents the intra-arterial blood pressure, V represents the arterial volume, Vm represents the maximum volume, and Vo represents the residual volume.

Solving for P(t) from Equation (1) at Pc=0 gives $$P(t) = -\frac{1}{k}\ln\left[\frac{V_m - V(t)}{V_m - V_o}\right] \tag{31}$$

Pm can therefore be determined by integration of Equation (13) to give $$P_m = \frac{1}{T}\int_0^T P(t)dt \tag{32}$$

where T is the heart beat period.

In the above development, it is assumed that V(t) is available. In practice, however, V(t) is obtained from the composite photoelectric plethysmography signal ($\hat{V}(t)$). $\hat{V}(t)$ contains an offset (B) due to absorption of the light of the photoelectric plethysmography apparatus by tissue, veins, capillaries, as well as other materials, all which contribute to the photoelectric plethysmography signal but are not the desired arterial blood.

Finger arterial blood volume assessment is an important issue in the present invention as well as other noninvasive blood pressure measurement techniques. It is primarily assumed that the Lambert-Beer's law can hold for arterial blood volume measurement in the finger using photoelectric plethysmograph technique.

Figure 4:
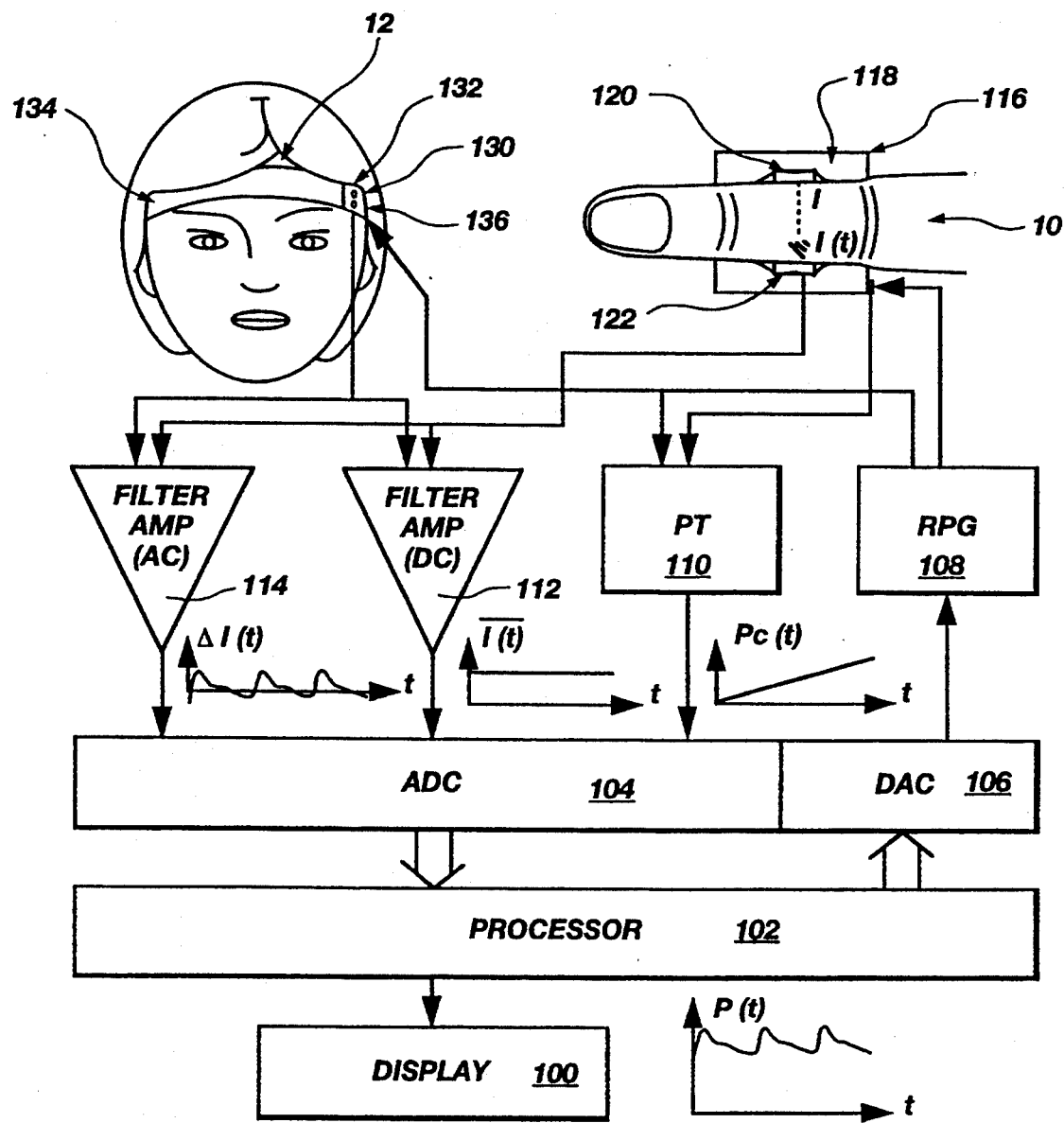
FIG. 4 is a block diagram of the presently preferred apparatus of the present invention.

Referring to the block diagram of FIG. 4, the incident light "beam" (I represented by line 124) of the LED 120 passes through the finger, generally designated at 10, to produce a time variant transmission light (I(t)) due to essentially arterial volume variation. The relationship can be described by the Lambert-Beer's law $$I(t) = Ie^{-\alpha[V(t)+V']} \tag{33}$$

where V(t) is blood volume contributed primarily by the arterial system and secondly by the venous and capillary systems due to red light absorption characteristic of oxygenated blood. When $Pc \geq 20$ mmHg, V(t) is dominated by the arterial system due to the collapse of the venous and capillary systems. The variable V' is tissue volume other than vascular systems; $\alpha$ is a composite absorption coefficient.

Figure 4A:
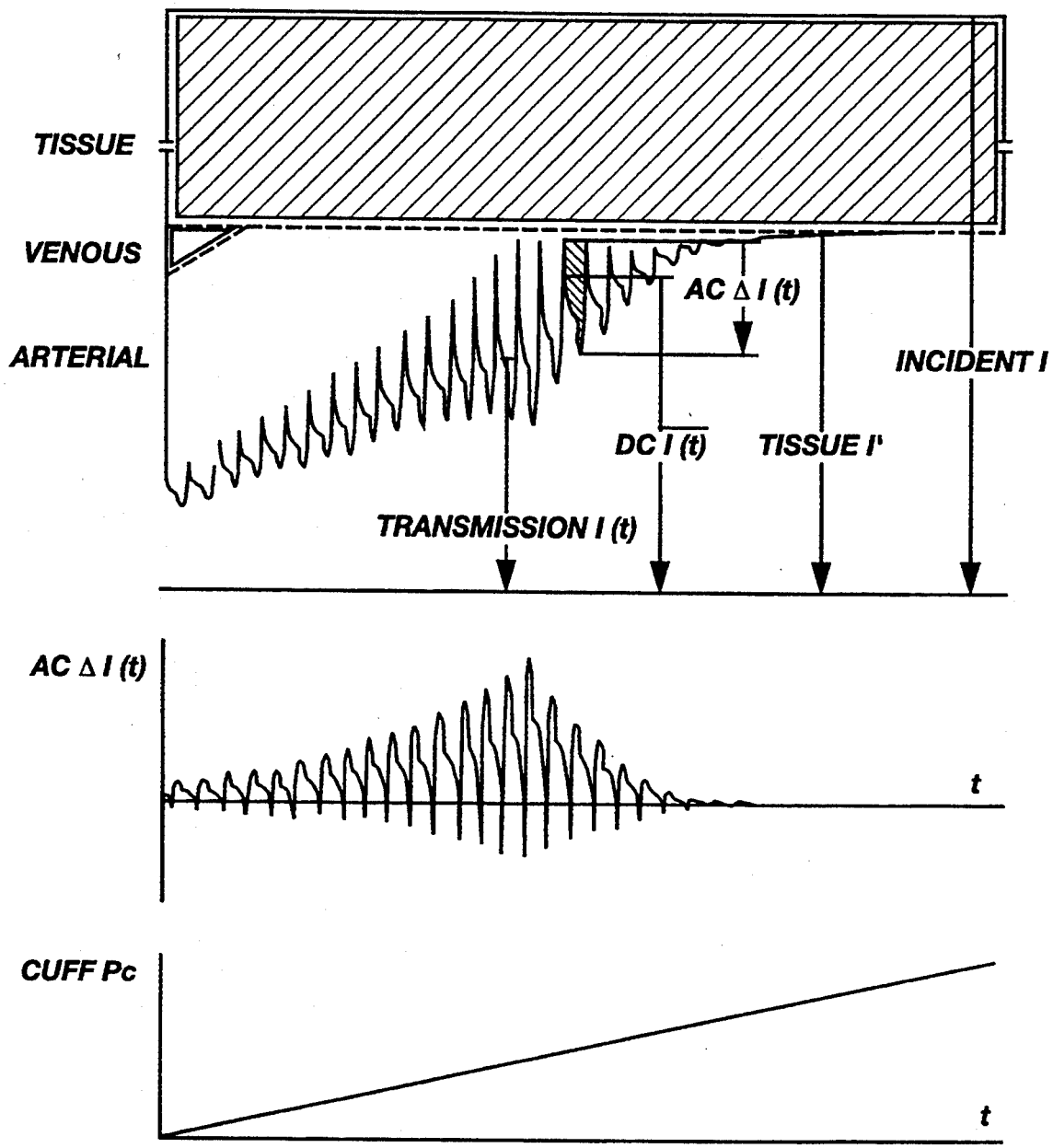
FIG. 4A is a diagram showing finger arterial measurement by photoelectric plethysmograph.

The magnitude of V(t) is usually about 1 to 5% of V' and varies according to the finger anatomic geometry. When the finger 10 is gradually compressed by a ramp Pc, I(t) will change as illustrated in FIG. 4A. FIG. 4A is a schematic diagram illustrating finger arterial volume measurement by photoelectric plethysmograph using the Lambert-Beer's law. In FIG. 4A, I represents incident light intensity, I' represents tissue transmission light intensity, I(t) represents finger transmission light intensity, $\Delta I(t)$ represents the AC component of I(t), $\overline{I(t)}$ represents the DC component of I(t), Pc represents the inflatable air bladder (118 and 132 in FIG. 4) pressure, and t represents time).

Assuming that the tissues other than vascular systems are incompressible, the venous and capillary systems are initially collapsed at very low Pc (about 5 and 20 mmHg, respectively) and then the blood volume in arterial system gradually decreases. When the arterial system is completely collapsed, the only optical absorption is from the tissues. The light intensity passes through the finger at this time is denoted as I'.

The relationship between V' and I' can also be described by the Lambert-Beer's law as follows.

$$I' = Ie^{-\alpha V'} \tag{34}$$

Equation (34) is a reduced form of Equation (33) when V(t) is zero. Substitution of Equation (34) into Equation (33) gives a relationship between V(t) and I(t) as follows.

$$I(t) = I'e^{-\alpha V(t)} \quad (35)$$

Equation (35) is a governing equation for producing AC and DC blood volume signals from the photoelectric plethysmograph measurement.

First, the AC blood volume signal is obtained by taking the derivative of I(t) with respect of V(t) to give $$\frac{dI(t)}{dV(t)} = -\alpha I(t) \quad (36)$$

Rearranging Equation (36) and replacing d (representing derivative) with $\Delta$ (representing AC signal) further gives $$\Delta V(t) = -\frac{\Delta I(t)}{\alpha I(t)} \quad (37)$$

Therefore, the AC blood volume signal ($\Delta V(t)$) can be obtained by the ratio of AC photoelectric plethysmograph ($\Delta I(t)$) over I(t). The magnitude of I(t) is essentially contributed by the DC component ($\overline{I(t)}$) of the photoelectric plethysmograph and can be approximated by $\overline{I(t)}$ within about 1 to 5% error as estimated by the fraction of blood to tissue volumes mentioned above.

Assuming very slow changes of DC values, the DC blood volume signal ($\overline{V(t)}$) also obeys Equation (35); note that Equation (35) also holds even if there is no pulse. Therefore $\overline{V(t)}$ is obtained as $$\overline{V(t)} = -\frac{1}{\alpha} \log\left[\frac{\overline{I(t)}}{I'}\right] \quad (38)$$

Considering an initial value (t=0) of the $\overline{V(t)}$ $$\overline{V(0)} = -\frac{1}{\alpha} \log\left[\frac{\overline{I(0)}}{I'}\right] \quad (39)$$

subtraction of Equation (39) from Equation (38) rearrangement and $$\overline{V(t)} = -\frac{1}{\alpha} \log\left[1 + \left(\frac{\overline{I(t)}}{\overline{I(0)}} - 1\right)\right] - \overline{V(0)} \quad (40)$$

Therefore the DC blood volume signal can be obtained by the log relationship of the transmission light intensity as described by the above equation.

In the continuous mode of the total compliance method, however, $\overline{I(t)}$ does not vary significantly from $\overline{I(0)}$ because a large variation ($\geq 20\%$) can trigger the calibration measurement where $\overline{V(t)}$ is not required. Accordingly, approximation of the log term in Equation (40) by a linear term can be made within error. The approximation and rearrangement give $$\overline{V(t)} = -\frac{1}{\alpha} \frac{\overline{I(t)}}{\overline{I(0)}} + \frac{1}{\alpha} - \overline{V(0)} \quad (41)$$

Consequently the total blood volume signal can be expressed by combination of both AC and DC signals as $$V(t) = G\{\hat{V}(t) - B\} \quad (42)$$

$$\hat{V}(t) = \overline{I(0)} \frac{\Delta I(t)}{I(t)} + \overline{I(t)}$$

$$G = -\frac{1}{\alpha \overline{I(0)}}$$

$$B = \alpha \overline{I(0)} \left[\frac{1}{\alpha} - \overline{V(0)}\right]$$

where ($\hat{V}(t)$) is a composite photoelectric plethysmograph signal which is used in the method of the present invention, G is a gain factor which is not specifically required by the method of the present invention, and B is an offset which can be determined by Equation (45), (51), provided below. The result of the relationship between $\hat{V}(t)$ and V(t) is given by $$V(t) = \hat{V}(t) - B \quad (43)$$

Since V(t) and $\hat{V}(t)$ have a linear relationship, $\Delta V$ as used in the above extraction for the model parameters (k, k', Vm, and Vo) and pressure values (Ps and Pd) are not affected by the value of B. Therefore the value of B can be determined by combining Equations (31) and (43) and substituting diastolic values for P, V, and $\hat{V}$ to give $$Pd = -\frac{1}{k} \ln\left[\frac{Vm - (\hat{V}d - B)}{Vm - Vo}\right] \quad (44)$$

and rearranging Equation (44) gives $$B = (Vm - Vo)e^{-kPd} - (Vm - \hat{V}d) \quad (45)$$

The presently preferred apparatus for carrying out the present invention will be described next.

The Presently Preferred Apparatus of the Present Invention

Provided in FIG. 4 is a block diagram of the presently preferred apparatus of the present invention. Desirably, the present invention can be readily adapted for use at a digital artery site or at a temporal artery site, as well as other sites, on a subject. The described apparatus is essentially the same for both finger, generally designated 10 in FIG. 4, site (digital artery) and forehead, generally designated 12 in FIG. 4, site (temporal artery) arrangements except for the construction of the structures which contact the subject. In the case of the finger site, a transmissive scheme is used. In the case of the forehead site, a reflective scheme is used. In the case of patients experiencing severe vasoconstriction, a forehead site may be a better site than a digital artery site.

Represented in FIG. 4 is a finger cuff 116 including an air bladder 118, whose structure will be explained further shortly, which is used to impose Pc on the artery. The finger cuff 116 includes an LED 120 and a photo-detector 122. The light emitted by the LED 120 (I in FIG. 4) is transmitted through the finger 10 and the light which is not absorbed by the body part is received by the photo-detector 122. The light "beam" travelling through the finger 10 is represented by a line 124. The intensity of the transmitted light (I(t)) received by the photo-detector 122 is modulated by the changing volume of the digital artery and represents the digital artery arterial volume plethysmography. Thus, from the output signal of the photo-detector 122 the arterial volume can be determined.

Those skilled in the art will appreciate the need for proper positioning of the LED 120 and photo-detector 122. One preferred position for these devices is on the opposite lateral sides of the middle phalanx of the finger 10. The signal output from the photo-detector, the I(t) signal, is fed to a DC filter amp 112 and to an AC filter amp 114 to separate the AC and DC components of the I(t) signal, referred to as the $\Delta I(t)$ signal and the $\overline{I(t)}$, respectively. The $\Delta I(t)$ signal and the $\overline{I(t)}$ signal are converted to digital values by an analog to digital convertor 104 for use and storage by the processor 102. The processor 102 is a microprocessor, and associated components, and the analog to digital convertor 104 are known in the art can be readily selected by those skilled in the art.

The illustrated structures provide one preferred example of a means for noninvasively detecting volume changes in an artery. Other structures, such as those which detect changes of arterial volume by sensing pressure changes or other parameters can also be used as the means for noninvasively detecting volume changes in an artery.

In order to obtain all of the parameters needed to carry out the total compliance model blood pressure determination, a ramp pressure generator 108 and a digital to analog converter 106 is provided and used to derive Pc. It will be appreciated that the ramp pressure generator 108 can apply a ramping pressure which is ramping upward or ramping downward. The ramp pressure generator can also provide a step increase or decrease in Pc.

The counter pressure (Pc) imposed at the finger site is measured by a pressure transducer 110 which produces an analog electrical signal which is conveyed to the analog to digital convertor 106 which provides corresponding digital values for processing and storage by the processor 102.

One preferred source for the ramp pressure generator 108, the pressure transducer, the LED 120, the photo-detector 122, and the filter amplifiers 112 and 114 components are those which are included in a device marketed under the FIN$\Delta$PRES TM trademark from Ohmeda. Another preferred source for the LED 120, the photo-detector 122, and the filter amplifiers 112 and 114 is from a commercially available pulse oximeter marketed under the trademark ASAT TM marketed by Baxter. Those skilled in the art will readily be able to provide the necessary interfaces to the digital to analog convertor 106 and the analog to digital convertor 104.

The processor controls the counter pressure (Pc) which is applied to the finger 10 via the digital to analog convertor 106. The processor 102 also collects the $\Delta I(t)$ signal, the $\overline{I(t)}$, and the Pc signals via the analog to digital convertor 104 and performs necessary computations in accordance with the previously described model and presents results to a visual display 100. It will be appreciated that the processor can also include output means for conveying the information to devices, other than a visual display, for storage, manipulation, or presentation.

The finger cuff 116, is also comprised of a cylinder of plastic material serving as the exterior cuff material. Latex material functions as the material for the air bladder 118. The selection of materials for the finger cuff 116 allows Pc to be applied when the air bladder 118 is inflated and nonocclusion of the artery when Pc is not imposed.

The finger cuff 116 is preferably constructed so that several sizes are available each to accommodate a different size patient finger. For example, finger cuff diameters of about 17, 22, and 27 mm will provide a finger cuff 116 suitable for most adults. The widths of the air bladders 118 are preferably 21, 28, and 34 mm, respectively. The dimension of each air bladder 118 is selected so that the width of the air bladder is equal to about 40% of the circumference of the finger at its midpoint in accordance with recommended industry practice for the dimensions of inflatable cuffs for use on the arm.

Also represented in FIG. 4 are structures which are applied to the patient's forehead 12. Represented in FIG. 4 is a forehead cuff, generally designated at 134, which includes an LED 130 and a photo-detector 136 which can be obtained from the same sources as LED 120 and photo-detector 122. The LED 130 and the photo-detector 136 are mounted about 5 mm apart in the forehead cuff so that the light emitted by the LED 130 will be reflected from the patient's tissue, including the blood of the temporal artery, and received by the photo-detector 136.

Also placed on the forehead cuff 134 is an inflatable air bladder 132 fabricated from thin-walled (0.1 mm) translucent polyurethane material having dimensions of 30 mm wide and 50 mm length. The forehead cuff 134 itself was made of soft, but unstretchable, nylon material 30 mm wide and having an adjustable length to fit to different head circumferences. The LED 130 and phototransducer 136 are preferably placed against a temporal superficial artery located on the forehead 12. The length of the forehead cuff 134 is adjusted to tightly embrace the air bladder 132, yet not restrict the inflation and deflation of the air bladder 132.

In FIG. 4, Pc(t) represents the cuff inflation pressure waveform, I represents the incident light transmitted into the finger 10, I(t) represents the photoelectric plethysmogram, $\Delta I(t)$ represents the AC plethysmograph waveform, $\overline{I(t)}$ represents the DC plethysmograph waveform, P(t) represents the blood pressure waveform, and t represents time.

Zeroing and linearity (from 0–200 mmHg) of the above described components should be within $\pm 1$ mmHg as known in the industry, for example, by using a pressure calibrator available under the trademark DELTA-CAL TM marketed by Utah Medical Products, Inc.

The processor 102, display 100, analog to digital convertor 104, and the digital to analog convertor 106 can preferably be carried out by an IBM-PC AT compatible computer equipped with a monitor, a math-coprocessor, and an ADC/DAC card, for example, one having eight 12-bit differential analog to digital channels and two digital to analog channels. The sampling frequency of the convertors is preferably 100 Hz.

When interfacing an IBM compatible computer functioning as the processor 102 to the analog to digital convertor 104, the following considerations should be recognized: (1) different gains for $\Delta I(t)$ and $\overline{I(t)}$ are necessary to obtain the maximum resolution of the analog to digital convertor since $\Delta I(t)$ is usually 1% to 5% of the magnitude of $\overline{I(t)}$; (2) the frequency response for $\Delta I(t)$ and $\overline{I(t)}$ should reduce any respiratory effects on the plethysmogram; and (3) the frequency response for ΔI(t) and $\overline{I(t)}$ should minimize any aliasing problem during the analog to digital conversion.

Figure 5:
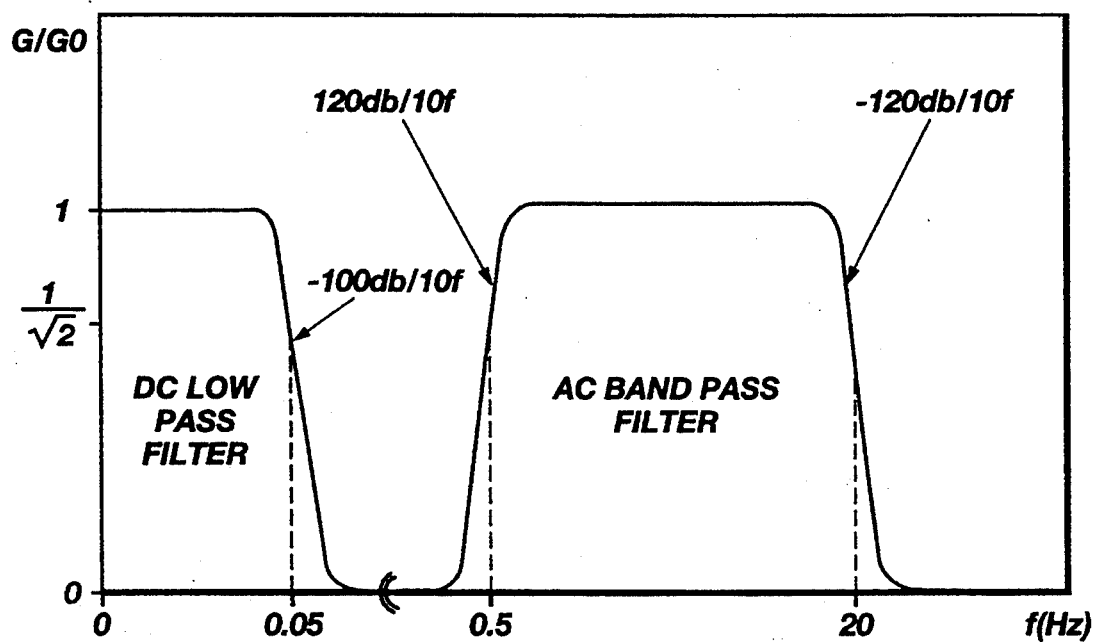
FIG. 5 is a chart showing the preferred frequency response of the amplifiers included in the apparatus of the present invention.

Provided in FIG. 5 is a chart representing the preferred frequency response. In FIG. 5, G represents gain and Go represents the maximum gain. The frequency response was chosen, using Fourier analysis calculations, to minimize respiratory effects. The major frequency components of the respiratory effect are in the range of 0.5–0.05 Hz for respiratory rates in the range of 3–30 min$^{-1}$. Therefore the respiratory effect in the above range can be effectively reduced by the filters. Since the preferred sampling rate is 100 Hz, which is five times as large as the higher cut-off frequency (fc=20 Hz) of the filters, the aliasing problem is sufficiently minimized according to the sampling theorem.

One preferred arrangement for providing the desired frequency response (low pass filter (fc=0.05 Hz)) utilizes a universal filter building block designated in the art as LTC1062 (Linear Technology) with a fifth order of all pole, maximal flat, and non-DC error characteristics. For the bandpass portion of the frequency response, a bandpass filter (low fc=0.5 Hz, high fc=20 Hz) using another universal filter building block designated in the art as LTC1061 (Linear Technology) with a sixth order bandpass function can preferably be used.

Having described one presently preferred apparatus for carrying out the present invention, it will be appreciated that many other structures can also be used to carry out the present invention. The presently preferred method of the present invention, which is intended to be used with the above described apparatus, will be explained next with the understanding that the method of the present invention can be used in many different circumstances and with many different apparatus.

The Presently Preferred Method of the Present Invention

Figure 6:
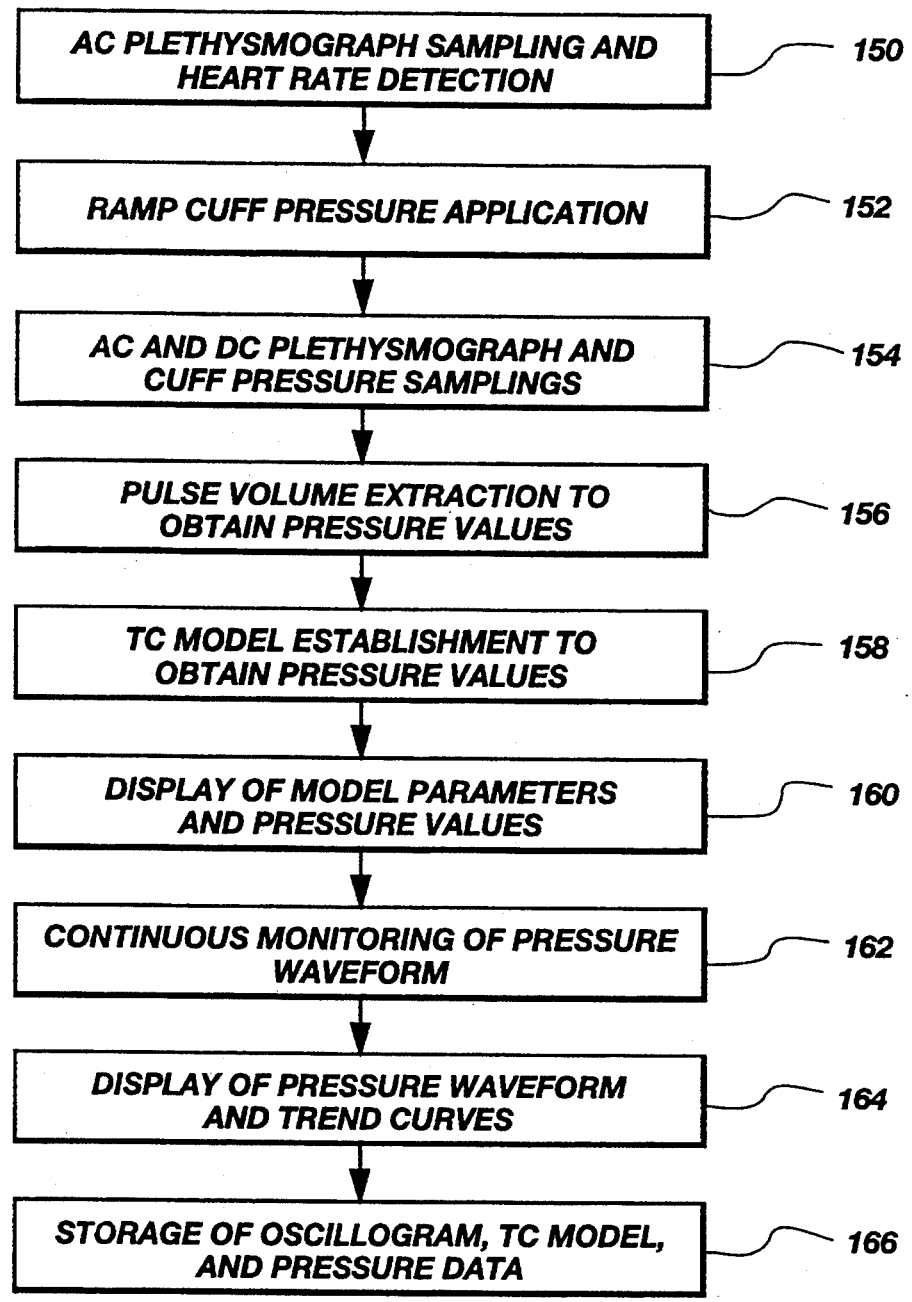
FIG. 6 is a flow chart illustrating one presently preferred method of the present invention.

FIG. 6 is a flow chart showing one presently preferred method of the present invention. It will be appreciated that the steps represented in FIG. 6 are carried out by the processor 102 (FIG. 4) by way of software which can be readily developed by those skilled in the art.

First, as shown at step 150 in FIG. 6, the sampling for an AC plethysmograph is taken and the patient heart rate is detected. Preferably, for a five second period, the ΔI(t) signal is sampled at a 100 Hz sampling rate in order to determine the patient's heart rate. Using the systolic and diastolic point information which can be obtained from the sampled signal, the beat to beat heart rate intervals are calculated.

Figure 7:
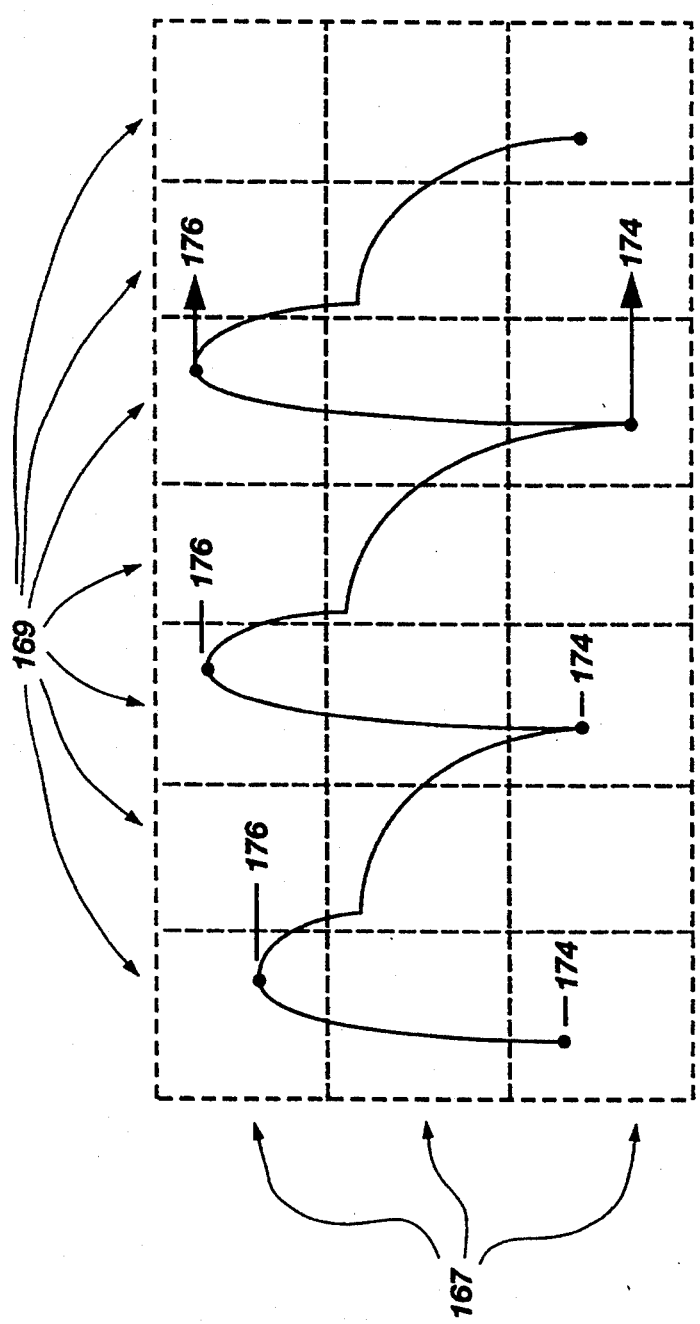
FIG. 7 is a chart showing the preferred criteria for heart rate detection.

To find the systolic and diastolic point information, the procedure represented in FIG. 7 is applied to the ΔI(t) signal. Represented in FIG. 7 are a plurality of time windows 167 (horizontal axis) and amplitude windows 169 (vertical axis). The time windows provide time tolerances for systolic point 176 and diastolic point 174 occurrences. The amplitude windows 169 provide amplitude tolerances for systolic and diastolic point occurrences. The overlap areas of the time and amplitude windows provided a more restrictive searching domain for systolic and diastolic points.

After the beat-to-beat heart rates are found, they are compared against each other. If the difference between any two heart rates is no more than 40%, the average of these heart rates are taken as a mean heart rate. Otherwise, another five second interval of the ΔI(t) signal is sampled. The steps are repeated until the criteria is satisfied.

Next, as represented at step 152, a ramp Pc signal is generated and pressure is begun to be applied to the air bladder 118 (FIG. 4). The Pc ramp rate is set in direct proportion to the heart rate. For example, if a patient's heart rate is 60/minute, then the Pc ramp rate is 5 mmHg/second. The Pc ramp rate design should be selected in order to collect enough, but compact, oscillogram data through a wide range of heart rates.

As represented at step 154, while the ramping Pc signal of step 152 is being applied, the AC plethysmography (ΔI(t)) and the DC plethysmography ($\overline{I(t)}$) signals, as well as the Pc signal associated therewith, are simultaneously sampled (100 Hz sampling rate) to the processor 102 (FIG. 4).

Next, as represented at step 156, the pulse volume is extracted to obtain a pulse oscillogram envelope. An AC volume signal (ΔV(t)), which is used as the volume oscillogram, is then calculated from the photoelectric plethysmography signals. Specifically, ΔV(t) constitutes the ratio $$\frac{\Delta I(t)}{\overline{I(t)}} \quad (46)$$

which was essentially derived from the Lambert-Beer's law as was explained earlier.

The ΔV(t) oscillations initially increase as Pc increases, then a maximum point is reached, followed by decreases. At the time when the ΔV(t) signal is decreased to below 5% of the maximum pulsation for three pulses, the ramp Pc signal is quickly terminated (0.5–1.0 second). Generally, the application of the ramp Pc signal will take about 30 seconds depending on the particular patient's Ps and heart rate.

After the ramp pressure signal has been terminated, the same steps for the heart rate detection are performed for this series of ΔV(t) oscillation signals. In this way, systolic and diastolic points are found with corresponding Pc.

Figure 8:
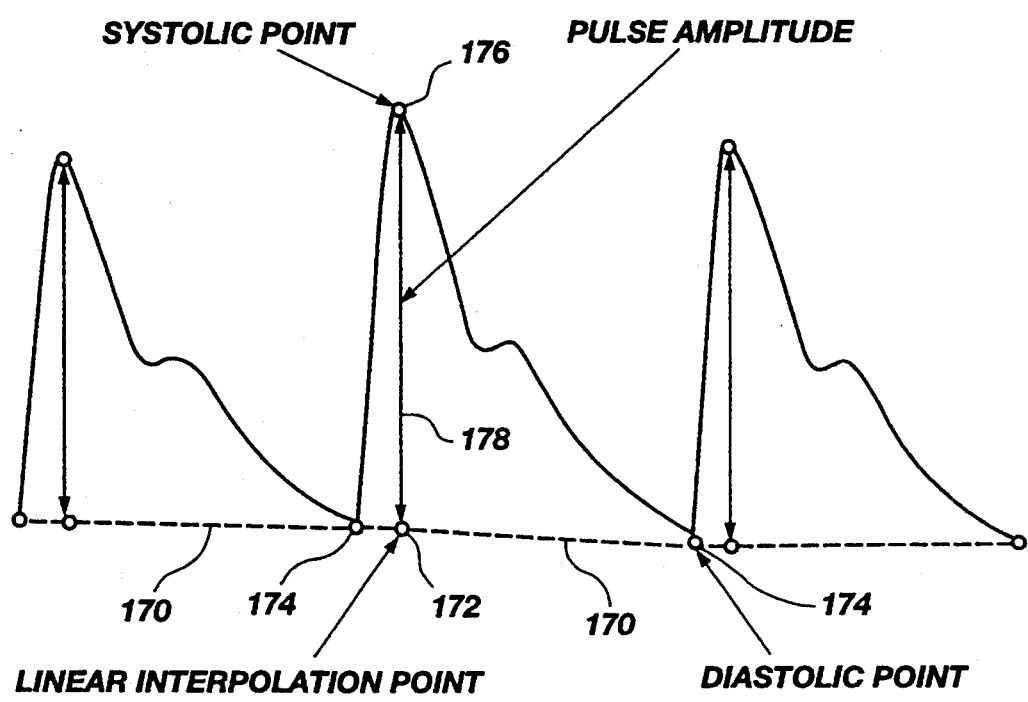
FIG. 8 is a diagram representing the pulse amplitude calculation used to establish an oscillogram envelope from the AC volume signal.

As included in step 156, to extract the oscillogram envelope, pulse amplitudes are calculated based on the obtained systolic and diastolic points. FIG. 8 shows how the pulse amplitude calculation is used to establish an oscillogram envelope from the AC volume signal (ΔV(t)). In FIG. 8, the dashed baseline 170 is a linear interpolation line between two adjacent diastolic points.

In the calculation, the baseline 170 is first established between two consecutive diastolic points 174 and linear interpolation points 172 are made on the baseline 170 corresponding to the same Pc of the systolic point 176 appearing within the two diastolic points 174. The amplitude difference between the systolic point 176 and the linear interpolation point 172 are the pulse amplitude for one heart beat. The same routine is then applied to the series of ΔV(t) in the oscillation signal.

Still referring to FIG. 8, the oscillogram envelope (ΔV(Pc)) is finally established by the envelope formed by this series of pulse amplitudes 178 (ΔV) each associated with their Pc value. Two criteria are used to refine the oscillogram envelope data. The first of these criteria is to reject the oscillogram envelope data for Pc<20 mmHg. The purpose of this criterion is to avoid venous and capillary effects on the arterial volume signal measured by the photoelectric plethysmography. The second of these two criteria is that each single oscillogram envelope point should not be 100% greater or less in amplitude than the immediately adjacent oscillogram envelope points. The purpose of this criterion is to reject the most motion artifacts and noise. Any data point which does not satisfy this criterion should be rejected.

Figure 9:
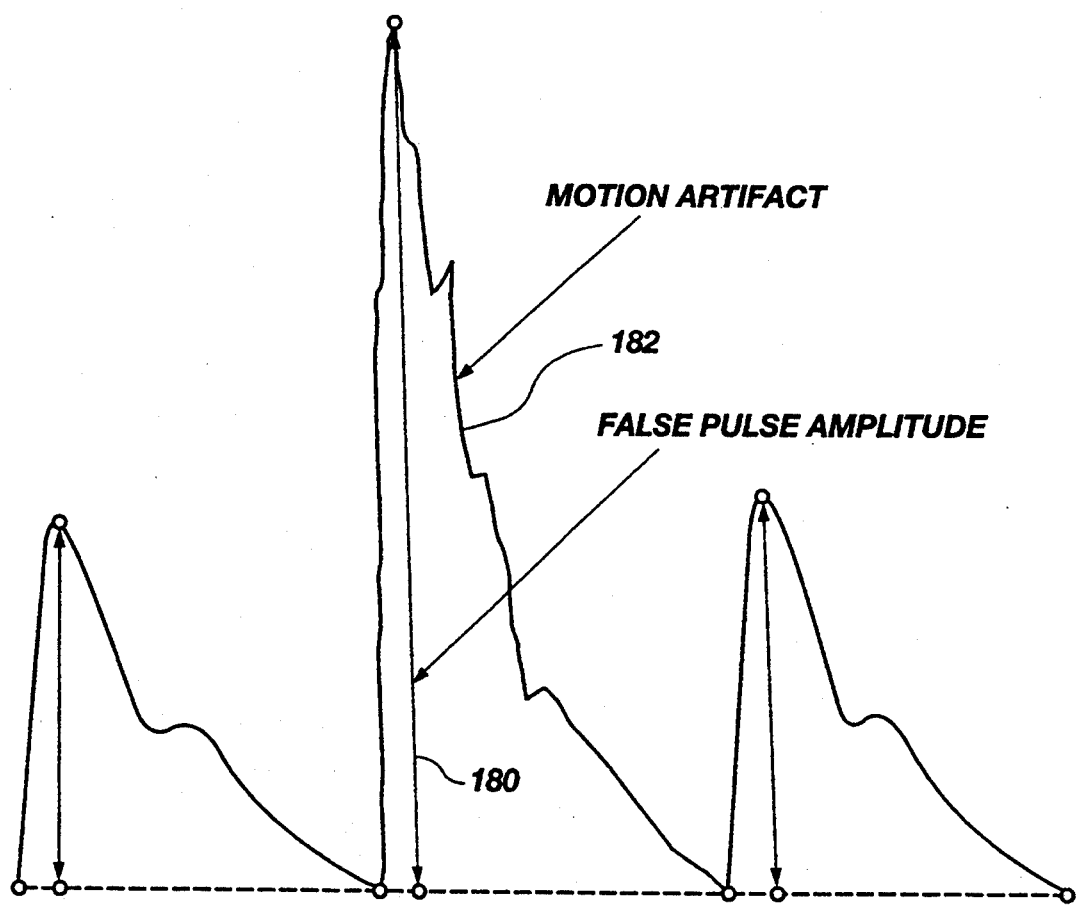
FIG. 9 is a diagram representing the rejection of a motion artifact.

An example of motion artifact rejection is shown in FIG. 9. In FIG. 9, a false pulse amplitude 180 caused by a motion artifact or noise 182 is at least 100% greater than its adjacent pulse amplitudes and, according to the criterion, is rejected.

Referring again to FIG. 6, the next step (158) is to establish the total compliance model for the patient and obtain the arterial pressure values for the patient. It will be appreciated the establishment of the total compliance model is a critical portion of the method of the present invention.

As described earlier, by fitting oscillogram envelope data to Equation (9) in the range of Pc≦Pd, the constants A and k can be obtained. Likewise, constants A' and k' are obtained by fitting oscillogram envelope data to Equation (12) in the range of Pc≧Ps. With the parameters A, A', k, and k' determined, the total compliance model parameters (Vm and Vo) and pressure values (Pd and ΔP) can be calculated from Equations (5), (10), (13), and (14). To minimize the effect of noise on the oscillogram envelope, Equation (14) is preferably extended to the whole applicable range of Pd<Pc<Ps using least square best fit criterion described above.

In the previous calculations, arbitrary assumptions were initially made that, in the oscillogram data ranges (Pc≦Pd, Pc≧Ps, and Pd<Pc<Ps), Pd and Ps were −15 mmHg and +30 mmHg of the Pc corresponding to the maximum volume pulsation. These assumptions were based on the observations known in the art that the Pc corresponding to maximum pulsation was near to Pm and that the difference between the Pm value and the Pd value is about ⅓ of ΔP. These assumptions are not expected to hold in any particular case and the estimates which result from these assumptions are not required to carry out the present invention. Still, these assumptions do provide an adequate starting point for the iterative approach in this embodiment of the present invention. Other approaches used to arrive at an estimation of Pd and Ps which can be used with the present invention, and which expedite the iterative approach to arrive at Ps and Pd, can be used.

The pressure values (Ps and Pd) along with the total compliance model parameters (Vm and Vo) are first calculated using the above described oscillogram data range assumptions. These new calculated pressure values (Ps and Pd) are then compared to the previous or assumed values and adjusted according to their error information. The previous pressure values are then updated by the current values. The calculations needed for the total compliance model and pressure value extraction are then repeated. This process is preferably continued until the errors between the current and previous pressure values are all within the standard of ±0.5 mmHg.

As shown at step 160 in FIG. 6, the total compliance model parameters, Vm and Vo, and pressure values, Ps and Pd, are determined after completion of the iterative process and then displayed on a visual display 100 (FIG. 4). Depending upon the oscillogram data points and noise level encountered, an average of about 30 seconds is needed to display the pressure values.

Once the total compliance model has been established, a continuous pressure waveform (P(t)) is then constructed, using Equation (31), from the volume waveform (V(t) with V(t)=ΔV(t)+$\overline{V(t)}$ where $\overline{V(t)}$ is the DC volume signal derived from the $\overline{I(t)}$ component).

In practice, it is preferred to constantly maintain a Pc of 20 mmHg in order to: 1) overcome the effect of venous and capillary blood on the arterial volume signal; and 2) hold the inflatable bladder in place so that the occurrence of motion artifacts are reduced. The constantly maintained PC of 20 mmHg is considered in the adjustment of Equation (31). Pm is determined by integration of the pressure waveform using Equation (32).

As represented in FIG. 6, the step of continuously monitoring the pressure waveform (step 162) is carried out. While the pressure waveform is continuously carried out, the pressure waveform, trend curves, and other useful information is desirably displayed (step 164). For example, P(t) can be continuously displayed and averages (over 15 seconds) of Ps, Pm, and Pd, as well as the patient's heart rate, are also displayed. It is preferred that digital values of these parameters also be displayed.

It is preferred in some circumstances that all of the collected raw data pertaining to the oscillogram, the total compliance model, variance analysis, and intermittent and continuous pressure measurement be stored in a data file for each individual patient. When stored in such a file, the incoming data should be tagged with the time when it is acquired.

The total compliance model described in Equations (1) and (2) is more specifically referred to as a single compartment total compliance model. The single compartment total compliance model of the present invention provides more accurate results than previously available models. A multi-compartment total compliance model can also be used to increase the accuracy of the measurements. The multi-compartment total compliance model is given by the form $$V = \begin{cases} Vm - (Vm - Vo)(A1e^{-k1P} + A2e^{-k2P} + \ldots + Ane^{-knP}), \\ \qquad\qquad\qquad\qquad\qquad\qquad\qquad\qquad\qquad P \geq 0 \\ Vo(A1'e^{-k1'P} + A2'e - k2'P + \ldots + An'e^{-kn'P}), P \leq 0 \end{cases} \quad (47)$$

To simplify representation, the transmural pressure ($P_T$) is replaced by P for Equation (47). Model parameters k1, k2, ..., kn are compliance indices of the multi-compartment model when P≧0; while k1', k2', ..., kn' are compliance indices when Ps0. Model coefficients A1, A2, ..., An and A1', A2', ..., An' correspond to the respective compartments and have the following relationships.

$$\begin{cases} A1 + A2 + \ldots + An = 1 \\ A1' + A2' + \ldots + An' = 1 \end{cases} \quad (48)$$

The derivatives of Equation (47) at P=0 give $$\frac{Vm - Vo}{Vo} = \frac{A1'k1' + A2'k2' + \ldots + An'kn'}{A1k1 + A2k2 + \ldots + Ankn} \quad (49)$$

It will be appreciated that the multi-compartment total compliance model will provide results which are improved over those obtained using the single compartment total compliance model. Under most circumstances, however, the accuracy of the single compartment total compliance model is adequate. As further investigation is conducted, the multi-compartment total compliance model may desirably be used in some circumstances.

Provided below are examples of the present invention in use and the results obtained thereby.

EXAMPLES

Clinical experiments were conducted on actual hospitalized patients. No particular criteria were used for patient selection. Thus, while nine intensive care unit patients were selected for the experiment, two were found not acceptable for use in the experiment. One patient had not already been provided with a device (catheter), as had the other patients, for providing direct arterial pressure measurement to use as a standard. The direct arterial pressure measurements were obtained by central arterial cannulation (descending aorta) which allowed continuous waveform and digital values of Ps, Pm, and Pd to be obtained using apparatus and methods well known in the art. Another of the nine patients was suffering from severe vasoconstriction making the finger site inappropriate for obtaining arterial volume data. The apparatus of the present invention, however, can be used even in patients suffering from severe vasoconstriction if another sensing site, e.g., the arm, is used. Characteristics of the seven patients on which the finger site apparatus represented in FIG. 4 was used are shown in Table 1.

TABLE 1

| Patient Identification | Gender | Age | Disease |
|---|---|---|---|
| CV | M | 60 | Splenectomy |
| WH | M | 55 | Acute Respiratory Failure |
| EB | F | 80 | Smoke Inhalation in Fire Accident |
| ED | M | 64 | Neuromuscular Respiratory Failure |
| SU | F | 53 | Acute Respiratory Failure |
| HD | M | 71 | Pulmonary Emboli |
| MC | F | 92 | Abdominal Annulism of Aorta |

Figure 10:
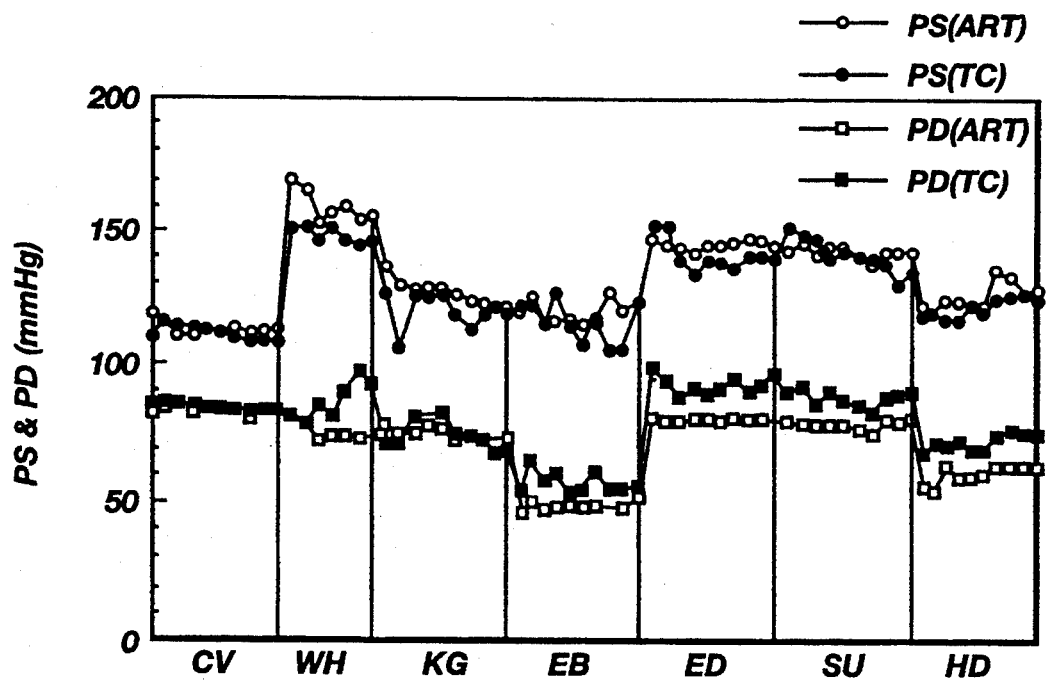
FIG. 10 is a diagram comparing the results obtained (systolic (Ps) and diastolic (Pd) pressures) using an apparatus embodying the present invention and the results obtained using direct central arterial blood pressure monitoring.
Figure 11:
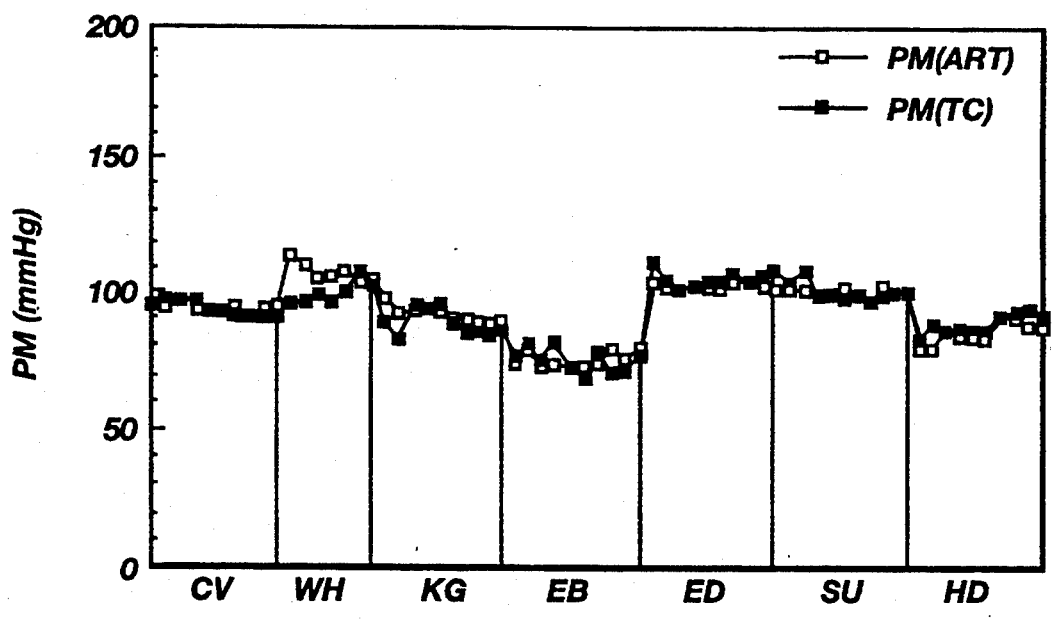
FIG. 11 is a diagram comparing the results obtained (mean arterial pressure (Pm)) using an apparatus embodying the present invention and the results obtained using direct central arterial blood pressure monitoring.

FIG. 10 shows the results of comparisons between the method of the present invention using the total compliance model (TC) and direct arterial cannulation (ART) for intermittent measurement of Ps and Pd. For clarity of presentation, the same comparison for continuous measurement of Pm is provided separately in FIG. 11.

Provided below in Table 2 are the differences between the mean of the pressure measurements using the apparatus of the present invention and the mean of the pressure measurements using the direct blood pressure measurement method. Also shown is the standard deviation (SD) of the measurements made using the apparatus of the present invention against the direct central arterial pressure measurement for the seven of the above-identified patients.

TABLE 2

| Patient | ΔPs Mean | ΔPs SD | ΔPm Mean | ΔPm SD | ΔPd Mean | ΔPd SD |
|---|---|---|---|---|---|---|
| CV | −1.0 | 5.7 | −1.2 | 2.2 | 1.2 | 2.6 |
| WH | −9.0 | 3.8 | −7.6 | 7.3 | 11.0 | 7.3 |
| KG | −5.3 | 6.3 | −4.1 | 4.9 | −0.9 | 4.9 |
| EB | −2.6 | 9.5 | −1.3 | 6.2 | 7.9 | 3.3 |
| ED | −1.9 | 5.1 | 2.7 | 2.8 | 13.5 | 3.0 |
| SU | −0.3 | 3.4 | 0.1 | 2.8 | 10.6 | 2.6 |
| HD | −3.2 | 3.4 | 2.9 | 1.8 | 12.5 | 1.7 |
| All Patient Average | −3.1 | 6.1 | −0.9 | 5.2 | 7.8 | 6.5 |

As can be observed from the data contained in Table 2, embodiments of the present invention results in pressure measurements which easily fall within the limits of proposed ANSI standards (5±8 mmHg) for noninvasive blood pressure measurements for all three pressures (Pd, Ps, and Pm). Moreover, an examination of interpatient variability shows that the interpatient components, $\Delta$, of the total patient variabilities, $SD_T$, are found to be considerably smaller (by more than one-half) for the method of the present invention than for the oscillometric method when applied to the same oscillogram data for all three pressures. In the case of As and Δm (corresponding to the Δ of Ps and Pm), the values of these parameters were significantly different at the $P<0.05$ level by F test, whereas the Δd (corresponding to the Δ of Pd) was not at $p=0.13$.

TABLE 3

| | Δ | | | δ | | |
|---|---|---|---|---|---|---|
| | Δs | Δm | Δd | δs | δm | δd |
| Method of the present invention (finger site) | 3.0 | 3.7 | 5.7 | 6.1 | 5.2 | 6.5 |
| Prior art oscillometric method (finger site | 7.3 | 9.5 | 11.4 | 8.1 | 10.9 | 11.9 |

Significantly, as can be seen from Table 3, the method of the present invention was found to be more accurate than the oscillometric method when applied to the finger in every situation except for the one parameter (Pd bias) for which the method and apparatus of the present invention did not meet the proposed ANSI standards. The Pd bias shown for the method and apparatus of the present invention is most likely due to a physiological bias resulting from difference in pressure at a digital artery and other pressure sensing sites on the body which has been demonstrated in the industry. As noted in Table 3, the measurements obtained using the oscillometric method fall quite short of meeting the proposed ANSI standards for noninvasive pressure measurement.

TABLE 4

| Method Mean | ΔPs | | | | ΔPm | | | | ΔPd | | | |
|---|---|---|---|---|---|---|---|---|---|---|---|---|
| | $SD_T$ | Δ | δ | Mean | $SD_T$ | Δ | δ | Mean | $SD_T$ | Δ | δ | Mean |
| Preferred embodiment (finger site) | −3.1 | 6.8 | 3.0 | 6.1 | −0.9 | 6.4 | 3.7 | 5.2 | 7.8 | 8.6 | 5.7 | 6.5 |
| Oscillometric (finger site) | −3.4 | 10.9 | 7.3 | 8.1 | −1.5 | 14.5 | 9.5 | 10.9 | 3.6 | 16.5 | 11.4 | 11.9 |
| Oscillometric (arm site) | −5.1 | 15.0 | 5* | 14.1 | 0.7 | 10.3 | 5* | 9.0 | 8.8 | 12.5 | 5* | 11.4 |

In Table 4, the column labeled "mean" provides the mean difference between the measurements obtained by the indicated method and a measurement obtained by a direct method, the column labeled $SD_T$ indicates the total patient variabilities, the column labeled Δ indicates inter-patient variabilities, the column labeled δ indicates intra-patient variabilities of the method of the present invention (finger site) and the oscillometric methods (finger and arm sites) for Ps, Pm, and Pd measurements. The ΔPs, ΔPm, and ΔPd reflect errors of Ps, Pm, and Pd with all pressure values in mmHg. In the case of the measurements obtained using the oscillometric method, different devices using the method were employed.

Most significant is the fact that the inter-patient variability, Δ, for the method and apparatus of the present invention is only about half of the Δ for the measurements obtained using the oscillometric method. This further supports the conclusion that the object of the present invention of being able to adapt to physiological variabilities of individual patients has been accomplished. Moreover, any differences between "actual" pressures and the measurements obtained using the present invention are likely due to differences in pressure at the different sensing sites (finger site versus brachial artery or descending aorta) and not due to the model employed by the present invention.

It will be appreciated that the present invention provides a noninvasive blood pressure measurement system and method which is more accurate on abnormal, as well as normal, patients than previously available noninvasive blood pressure monitoring devices and methods. The present invention also provides a noninvasive blood pressure measurement system and method which utilizes a physiologically based model rather than an empirically based model and which results in little inter-patient variability. Furthermore, the present invention provides a noninvasive blood pressure measurement system and method which allows sensing at any one of a number of sites on the patient, such as a finger, and is suitable for long term monitoring.

The present invention may be embodied in other specific forms without departing from its spirit or essential characteristics. The described embodiment is to be considered in all respects only as illustrative and not restrictive.

The scope of the invention is, therefore, indicated by the appended claims rather than by the foregoing description. All changes which come within the meaning and range of equivalency of the claims are to be embraced within their scope.

What is claimed and desired to be secured by United States Letters patent is:

1. An apparatus for automatically and noninvasively monitoring the blood pressure of patients having either normal or abnormal blood pressure levels or blood pressure waveforms, the apparatus comprising:
    means for noninvasively detecting volume changes in an artery of the patient and for generating a volume signal;
    pressure means for applying counter pressure to the artery;
    processor means, electrically coupled to the means for noninvasively detecting volume changes and the pressure means, for coordinating the operation of each said means in relation to one another and for deriving from the variations in the volume signal accompanied by at least intermittent application of counter pressure to the artery by the pressure means at least the following parameters: (1) maximum volume of the artery, (2) residual volume of the artery, and (3) at least a first compliance value and a second compliance value, the first compliance value representing the compliance of the artery wall to changes of pressure exerted by the blood contained therein when the transmural pressure is greater than zero and the second compliance value representing the compliance of the artery wall to changes of pressure exerted by the blood contained therein when the transmural pressure is less than zero, the maximum volume of the artery, the residual volume of the artery, and the compliance values being used to noninvasively determine the actual blood pressure within the artery; and
    output means for receiving information from the processor means.

2. An apparatus for automatically and noninvasively monitoring the blood pressure of patients as defined in claim wherein the means for noninvasively detecting volume changes in an artery of the patient comprises:
    light means for passing a light beam into a body part of said subject containing an arterial blood vessel; and
    detection means for detecting the amount of said light beam absorbed by blood in the blood vessel.

3. An apparatus for automatically and noninvasively monitoring the blood pressure of patients as defined in claim 2 wherein the light means comprises a light source positioned to emit light into the subject's body part and wherein the detection means comprises a photo detector positioned to receive the light not absorbed by the blood in the blood vessel.

4. An apparatus for automatically and noninvasively monitoring the blood pressure of patients as defined in claim 3 wherein the photo detector is positioned to receive light transmitted through the body part.

5. An apparatus for automatically and noninvasively monitoring the blood pressure of patients as defined in claim 3 wherein the photo detector is positioned to receive light reflected from the body part.

6. An apparatus for automatically and noninvasively monitoring the blood pressure of patients as defined in claims 4 or 5 wherein the light source comprises a semiconductor light emitting source and wherein the photo detector comprises a semiconductor light sensing device.

7. An apparatus for automatically and noninvasively monitoring the blood pressure of patients as defined in claim wherein the pressure means comprises:
    an inflatable air bladder configured to apply pressure to a body part; and
    a pressure generator connected to the inflatable bladder and being controlled by the processor means.

8. An apparatus for automatically and noninvasively monitoring the blood pressure of patients as defined in claim wherein the processor means comprises:
    a microprocessor;
    at least one analog to digital convertor interfacing the detection means and microprocessor; and
    at least one digital to analog convertor interfacing the microprocessor and the pressure means.

9. An apparatus for automatically and noninvasively monitoring the blood pressure of patients as defined in claim 1 wherein the output means comprises a visual monitor.

10. A system for noninvasively measuring arterial blood pressure of a subject, the system comprising:
    light means for passing a light beam into a body part of said subject containing an arterial blood vessel;
    detection means for detecting the amount of said light beam absorbed by blood in the blood vessel;

pressure means for applying counter pressure to the arterial blood vessel;

processor means, electrically coupled to the light means, the detection means and the pressure means, for coordinating the operation of each said means in relation to one another and for deriving from the variations in the detected light beam accompanied by at least intermittent application of counter pressure to the artery by the pressure means the maximum volume of the artery, the residual volume of the artery, and at least a first compliance of the artery wall to changes of pressure contained therein and a second compliance of the artery wall to changes of pressure contained therein, the first compliance representing the compliance of the artery wall to changes of pressure exerted by the blood contained therein when the transmural pressure is greater than zero and the second compliance representing the compliance of the artery wall to changes of pressure exerted by the blood contained therein when the transmural pressure is less than zero, the maximum volume of the artery, the residual volume of the artery, the first compliance of the artery wall to pressure changes, and the second compliance of the artery wall to pressure changes both being used to noninvasively determine the actual blood pressure within the artery; and display means, electrically coupled to the processor means, for outputting a visually perceptible indication of the subject's arterial blood pressure.

11. A system for noninvasively measuring arterial blood pressure of a subject as defined in claim 10 wherein the light means comprises a light source positioned to emit light into the subject's body part and wherein the detection means comprises a photo detector positioned to receive the light not absorbed by the blood in the blood vessel.

12. A system for noninvasively measuring arterial blood pressure of a subject as defined in claim 11 wherein the photo detector is positioned to receive light transmitted through the body part.

13. A system for noninvasively measuring arterial blood pressure of a subject as defined in claim 11 wherein the photo detector is positioned to receive light reflected from the body part.

14. A system for noninvasively measuring arterial blood pressure of a subject as defined in claim as defined in claims 12 or 13 wherein the light source comprises a semiconductor light emitting source and wherein the photo detector comprises a semiconductor light sensing device.

15. A system for noninvasively measuring arterial blood pressure of a subject as defined in claim 10 wherein the pressure means comprises:

an inflatable air bladder; and a pressure generator connected to the inflatable bladder and being controlled by the processor means.

16. A system for noninvasively measuring arterial blood pressure of a subject as defined in claim 15 wherein the inflatable bladder is configured to substantially encircle the body part.

17. A system for noninvasively measuring arterial blood pressure of a subject as defined in claim 15 wherein the inflatable bladder is configured to impose a planar pressure on the body part.

18. A system for noninvasively measuring arterial blood pressure of a subject as defined in claim 17 wherein the body part is the forehead of the subject and the detection means comprises a photo detector which is positioned to receive light reflected from the body part.

19. A system for noninvasively measuring arterial blood pressure of a subject as defined in claim 10 wherein the processor means comprises:

a microprocessor;

at least one analog to digital convertor interfacing the detection means and microprocessor; and at least one digital to analog convertor interfacing the microprocessor and the pressure means.

20. A system for noninvasively measuring arterial blood pressure of a subject as defined in claim 10 wherein the processor means utilizes the intermittent application of counter pressure to the artery by the pressure means the maximum volume of the artery, the residual volume of the artery, and the compliance of the artery wall to changes of pressure contained therein to noninvasively determine the actual blood pressure within the artery in accordance with $$k' = \frac{Vm - Vo}{Vo} k$$

where Vm is the maximum volume of the artery, Vo is the residual volume of the artery, and k and k' are compliance indices.

21. A system for noninvasively measuring arterial blood pressure of a subject as defined in claim 10 wherein the display means comprises a video monitor.

22. A method for noninvasively measuring arterial blood pressure of a subject, the method comprising the steps of:

(a) passing a light beam into a body part of said subject containing an arterial blood vessel;

(b) detecting the amount of said light beam absorbed by blood in the blood vessel;

(c) applying counter pressure to the arterial blood vessel;

(d) coordinating the operation of passing a light beam, detecting the amount of said light beam absorbed, and applying the counter pressure;

(e) deriving from the variations in the detected light beam, such variations corresponding to changes in the volume of said artery, accompanied by the intermittent application of counter pressure to the artery, the artery's residual volume, the artery wall's compliance to changes of pressure contained therein when the transmural pressure is greater than zero, the artery wall's compliance to changes of pressure contained therein when the transmural pressure is less than zero, and the artery's maximum volume, (f) calculating the actual blood pressure within the artery using the maximum volume of the artery, the residual volume of the artery, the compliance of the artery wall to pressure changes when the transmural pressure is greater than zero, and the compliance of the artery wall when the transmural pressure is less than zero; and (g) outputting the actual blood pressure within the artery to an electrical device such that the actual blood pressure can be processed, stored, or displayed.

23. A method for noninvasively measuring arterial blood pressure of a subject as defined in claim 22 wherein the step of passing a light beam into a body part comprises the step of passing a light beam through a body part and the step of detecting the amount of said light beam absorbed comprises the step of detecting the amount of said light beam which is transmitted through the body part.

24. A method for noninvasively measuring arterial blood pressure of a subject as defined in claim 22 wherein the step of passing a light beam into a body part comprises the step of emitting a light beam into a body part and the step of detecting the amount of said light beam absorbed comprises the step of detecting the amount of said light beam which is reflected from the body part.

25. A method for noninvasively measuring arterial blood pressure of a subject as defined in claim 22 wherein the step of coordinating the operation comprises the step carrying out steps (a) through (g) during a calibration interval and the step of carrying out steps (a) through (b) and (e) through (g) during a monitoring interval.

26. A method for noninvasively measuring arterial blood pressure of a subject as defined in claim 22 wherein method further comprises repeating steps (a) through (b) and (e) through (g).

27. A method for noninvasively measuring arterial blood pressure of a subject as defined in claim 22 wherein the step of applying counterpressure comprises the step of ramping the pressure upward from less than the diastolic pressure of the artery to greater than the systolic pressure of the artery.

28. A method for noninvasively measuring arterial blood pressure of a subject as defined in claim 22 wherein the step of calculating the actual blood pressure within the artery comprises the step of substantially performing the calculation $$k' = \frac{Vm - Vo}{Vo} k$$

where Vm is the maximum volume of the artery, Vo is the residual volume of the artery, and k and k' are compliance indices.

29. A method for noninvasively measuring arterial blood pressure of a subject as defined in claim 22 wherein the step of outputting the actual blood pressure comprises the step of outputting the actual blood pressure to a visual display device.

30. An apparatus for automatically and noninvasively monitoring the blood pressure of patients having either normal or abnormal blood pressure levels or blood pressure waveforms, the apparatus comprising:

means for noninvasively detecting volume changes in an artery of the patient and for generating a volume signal;

pressure means for applying counter pressure to the artery;

first means, electrically coupled to the means for noninvasively detecting volume changes and the pressure means, for deriving from the variations in the volume signal accompanied by the intermittent application of counter pressure to the artery by the pressure means at least the following parameters: (1) maximum volume of the artery, (2) residual volume of the artery, and (3) a first compliance of the artery wall to changes of pressure exerted by the blood contained therein when the transmural pressure is greater than zero, the maximum volume of the artery, the residual volume of the artery, and the first compliance of the artery wall to pressure changes being used to noninvasively determine at least a portion of the information needed to calculate pressure within the artery;

second means, electrically coupled to the means for noninvasively detecting volume changes and the pressure means, for deriving from the variations in the volume signal accompanied by the intermittent application of counter pressure to the artery by the pressure means at least the following parameters: (1) maximum volume of the artery, (2) residual volume of the artery, and (3) a second compliance of the artery wall to changes of pressure exerted by the blood contained therein when the transluminal pressure is less than zero, the maximum volume of the artery, the residual volume of the artery, and the second compliance of the artery wall to pressure changes being used to noninvasively determine at least a portion of the information needed to calculate the pressure within the artery; and output means for receiving information from the first means for deriving and the second means for deriving.

31. An apparatus for automatically and noninvasively monitoring the blood pressure of patients having either normal or abnormal blood pressure levels or blood pressure waveforms as defined in claim 30 wherein the first means for deriving and the second means for deriving comprise a processor means.

32. An apparatus for automatically and noninvasively monitoring the blood pressure of patients having either normal or abnormal blood pressure levels or blood pressure waveforms as defined in claim 31 wherein the processor means comprises a microprocessor.

* * * * *